(12) United States Patent
Weiss et al.

(10) Patent No.: US 12,351,764 B2
(45) Date of Patent: Jul. 8, 2025

(54) METHOD FOR THE TREATMENT OF PLASTIC PYROLYSIS OILS INCLUDING SINGLE-STAGE HYDROCRACKING

(71) Applicants: IFP Energies nouvelles, Rueil-Malmaison (FR); REPSOL S.A., Madrid (ES)

(72) Inventors: Wilfried Weiss, Rueil-Malmaison (FR); Jérôme Bonnardot, Rueil-Malmaison (FR); Iñigo Ribas Sangüesa, Mostoles (ES)

(73) Assignees: IFP Energies nouvelles, Rueil-Malmaison (FR); REPSOL S.A., Madrid (ES)

( * ) Notice: Subject to any disclaimer, the term of this patent is extended or adjusted under 35 U.S.C. 154(b) by 137 days.

(21) Appl. No.: 18/018,170

(22) PCT Filed: Jul. 26, 2021

(86) PCT No.: PCT/EP2021/070849
§ 371 (c)(1),
(2) Date: Jan. 26, 2023

(87) PCT Pub. No.: WO2022/023262
PCT Pub. Date: Feb. 3, 2022

(65) Prior Publication Data
US 2023/0272292 A1    Aug. 31, 2023

(30) Foreign Application Priority Data
Jul. 30, 2020   (FR) ...................................... 2008106

(51) Int. Cl.
*C10G 65/12*   (2006.01)
*B01D 3/14*    (2006.01)
(Continued)

(52) U.S. Cl.
CPC ............... *C10G 65/12* (2013.01); *B01D 3/14* (2013.01); *B01D 3/38* (2013.01); *B01J 21/04* (2013.01);
(Continued)

(58) Field of Classification Search
None
See application file for complete search history.

(56) References Cited

U.S. PATENT DOCUMENTS 3,492,220 A * 1/1970 Lempert ................ C10G 45/36
                                                    208/210
3,556,987 A * 1/1971 Zimmerman, Jr. .... C10G 61/06
                                                    208/53
(Continued)

FOREIGN PATENT DOCUMENTS

WO   WO-2014001632 A1 *  1/2014 ............. C10B 53/02
WO   WO-2020252228 A1 * 12/2020 ............. C10B 49/22

OTHER PUBLICATIONS

International Search Report PCT/EP2021/070849 dated Oct. 14, 2021 (pp. 1-2).

*Primary Examiner* — In Suk C Bullock
*Assistant Examiner* — Alyssa L Cepluch
(74) *Attorney, Agent, or Firm* — Csaba Henter; Millen, White, Zelano & Branigan, P.C.

(57) ABSTRACT

The present invention relates to a process for treating a plastics pyrolysis oil, comprising:
  a) selective hydrogenation of said feedstock in the presence of at least hydrogen and of at least one selective hydrogenation catalyst;
  b) hydrotreatment of said hydrogenated effluent in the presence of at least hydrogen and of at least one hydrotreatment catalyst, to obtain a hydrotreated effluent;

(Continued)

c) hydrocracking of said hydrotreated effluent in the presence of at least hydrogen and of at least one hydrocracking catalyst, to obtain a hydrocracked effluent;

d) separation of the hydrocracked effluent in the presence of an aqueous stream, at a temperature of between 50 and 370° C., to obtain at least one gaseous effluent, an aqueous liquid effluent and a hydrocarbon-based liquid effluent.

14 Claims, 2 Drawing Sheets

(51) Int. Cl.
| | | |
|---|---|---|
| B01D 3/38 | (2006.01) | |
| B01J 21/04 | (2006.01) | |
| B01J 23/883 | (2006.01) | |
| B01J 29/076 | (2006.01) | |
| C07C 4/06 | (2006.01) | |
| C10G 1/00 | (2006.01) | |
| C10G 1/10 | (2006.01) | |

(52) U.S. Cl.
CPC ........... *B01J 23/883* (2013.01); *B01J 29/076* (2013.01); *C07C 4/06* (2013.01); *C10G 1/002* (2013.01); *C10G 1/10* (2013.01); *C10G 2300/1003* (2013.01); *C10G 2300/1092* (2013.01); *C10G 2300/301* (2013.01); *C10G 2400/02* (2013.01)

(56) References Cited

U.S. PATENT DOCUMENTS

| | | | |
|---|---|---|---|
| 4,498,972 | A | 2/1985 | Toulhoat et al. |
| 4,510,042 | A | 4/1985 | Billon et al. |
| 4,818,743 | A | 4/1989 | Simpson et al. |
| 4,895,995 | A * | 1/1990 | James, Jr. ............... A62D 3/37 208/262.5 |
| 5,089,463 | A | 2/1992 | Johnson |
| 5,221,656 | A | 6/1993 | Clark et al. |
| 5,622,616 | A | 4/1997 | Porter et al. |
| 5,827,421 | A | 10/1998 | Sherwood, Jr. |
| 5,969,201 | A | 10/1999 | Kalnes et al. |
| 6,332,976 | B1 | 12/2001 | Mignard et al. |
| 6,589,908 | B1 | 7/2003 | Ginestra et al. |
| 7,119,045 | B2 | 10/2006 | Magna et al. |
| 2007/0080099 | A1 | 4/2007 | Reid et al. |
| 2015/0001061 | A1* | 1/2015 | Bordynuik ............... C10L 1/06 202/112 |
| 2016/0264874 | A1* | 9/2016 | Narayanaswamy ..... C10G 1/10 |
| 2018/0155633 | A1* | 6/2018 | Al-Ghamdi ............ C10G 9/005 |
| 2019/0161683 | A1 | 5/2019 | Narayanaswamy et al. |
| 2020/0261875 | A1 | 8/2020 | Plais et al. |
| 2021/0189248 | A1* | 6/2021 | Timken ................. C10G 1/002 |

* cited by examiner

METHOD FOR THE TREATMENT OF PLASTIC PYROLYSIS OILS INCLUDING SINGLE-STAGE HYDROCRACKING

TECHNICAL FIELD

The present invention relates to a process for treating a plastics pyrolysis oil so as to obtain a hydrocarbon-based effluent which can be upgraded, for example by being at least partly incorporated directly into a naphtha or diesel pool or as feedstock for a steam cracking unit. More particularly, the present invention relates to a process for treating a feedstock obtained from the pyrolysis of plastic waste, so as to at least partly remove impurities, notably olefins (monoolefins and diolefins), metals, in particular silicon, and halogens, in particular chlorine, which said feedstock may contain in relatively large amounts, and so as to hydrogenate the feedstock to be able to upgrade it.

The process according to the invention thus makes it possible to treat the plastics pyrolysis oils to obtain an effluent which can be totally or partly injected into a steam cracking unit. The process according to the invention thus makes it possible to upgrade the plastics pyrolysis oils, while at the same time reducing coke formation and thus the risks of clogging and/or of premature loss of activity of the catalyst(s) used in the steam cracking unit, and reducing the corrosion risks.

PRIOR ART

Plastics obtained from collection and sorting channels may undergo a step of pyrolysis so as to obtain, inter alia, pyrolysis oils. These plastics pyrolysis oils are generally burnt to generate electricity and/or used as fuel in industrial boilers or urban heating.

Another route for upgrading plastics pyrolysis oils is the use of these plastics pyrolysis oils as feedstock for a steam cracking unit so as to (re)create olefins, said olefins being constituent monomers of certain polymers. However, plastic waste is generally mixtures of several polymers, for example mixtures of polyethylene, polypropylene, polyethylene terephthalate, polyvinyl chloride and polystyrene. Furthermore, depending on the applications, the plastics may contain, in addition to polymers, other compounds, such as plasticizers, pigments, colorants or polymerization catalyst residues. Plastic waste may also contain, in minor amount, biomass originating, for example, from household waste. As a result, the oils obtained from the pyrolysis of plastic waste comprise a lot of impurities, in particular diolefins, metals, notably silicon, or halogenated compounds, notably chlorine-based compounds, heteroelements such as sulfur, oxygen and nitrogen, and insoluble matter, in contents that are often high and incompatible with steam cracking units or units located downstream of the steam cracking units, notably polymerization processes and selective hydrogenation processes. These impurities may give rise to operability problems and notably problems of corrosion, coking or catalytic deactivation, or alternatively incompatibility problems in the applications of the target polymers. The presence of diolefins may also lead to problems of instability of the pyrolysis oil, characterized by the formation of gums. The gums and the insoluble matter that may be present in pyrolysis oil can give rise to problems of clogging in the processes.

Furthermore, during the steam cracking step, the yields of light olefins sought for petrochemistry, notably ethylene and propylene, depend greatly on the quality of the feedstocks sent for steam cracking. The BMCI (Bureau of Mines Correlation Index) is often used to characterize hydrocarbon cuts. Globally, the yields of light olefins increase when the paraffin content increases and/or when the BMCI decreases. Conversely, the yields of undesired heavy compounds and/or of coke increase when the BMCI increases.

WO 2018/055555 proposes an overall process for recycling plastic waste, which is very general and relatively complex, ranging from the very step of pyrolysis of the plastic waste up to the steam cracking step. The process of patent application WO 2018/055555 comprises, inter alia, a step of hydrotreating the liquid phase obtained directly from the pyrolysis, preferably under quite stringent conditions notably in terms of temperature, for example at a temperature of between 260 and 300° C., a step of separation of the hydrotreatment effluent and then a step of hydrodealkylation of the heavy effluent separated out, preferably at a high temperature, for example between 260 and 400° C.

The unpublished patent application FR 20/01758 describes a process for treating a plastics pyrolysis oil, comprising:
   a) selective hydrogenation of said feedstock in the presence of hydrogen and of a selective hydrogenation catalyst to obtain a hydrogenated effluent;
   b) hydrotreatment of said hydrogenated effluent in the presence of hydrogen and of a hydrotreatment catalyst, to obtain a hydrotreatment effluent;
   c) separation of the hydrotreatment effluent in the presence of an aqueous stream, at a temperature of between 50 and 370° C., to obtain a gaseous effluent, an aqueous liquid effluent and a hydrocarbon-based liquid effluent;
   d) optionally, a step of fractionation of all or part of the hydrocarbon-based effluent obtained from step c), to obtain a gas stream and at least two hydrocarbon-based streams which may be a naphtha cut and a heavier cut;
   e) a recycling step comprising a phase of recovering a fraction of the hydrocarbon-based effluent obtained from the separation step c) or a fraction of and/or at least one of the hydrocarbon-based streams obtained from the fractionation step d), into the selective hydrogenation step a) and/or the hydrotreatment step b).

According to patent application FR 20/01758, the naphtha cut obtained from the fractionation step may be totally or partly sent either to a steam cracking unit or to a naphtha pool obtained from conventional petroleum feedstocks, or may be recycled into step e).

The heavier cut obtained from the fractionation step may be totally or partly sent either to a steam cracking unit or to a diesel or kerosene pool obtained from conventional petroleum feedstocks, or may be recycled into step e).

Although the heavier cut can be sent to a steam cracking unit, few refiners favour this option. The reason for this is that the heavier cut has a high BMCI and contains, relative to the naphtha cut, more naphthenic, naphtheno-aromatic and aromatic compounds, thus leading to a higher C/H ratio. This high ratio is a cause of coking in the steam cracker, thus requiring steam cracking furnaces dedicated to this cut. Furthermore, the steam cracking of such a heavy cut produces a smaller amount of products of interest which are notably ethylene and propylene, but more pyrolysis gasoline.

It would thus be advantageous to minimize the yield of the heavy cut and to maximize the yield of the naphtha cut by transforming the heavy cut at least partly into naphtha cut by hydrocracking. This makes it possible to obtain more naphtha which is preferably sent for steam cracking to produce more olefins while at the same time reducing, in particular, the risks of clogging during steps of treatment of plastics pyrolysis oils, such as those described in the prior art, and coke formation in large amounts and/or the corrosion risks encountered during subsequent step(s), for example during the step of steam cracking of the plastics pyrolysis oils. The heavy cut that has not been transformed by hydrocracking is, for its part, preferably upgraded by recycling it into the hydrocracking step so as to be recracked. Furthermore, the C2 to C4 compounds produced during the hydrocracking may also be sent for steam cracking, which makes it possible to improve the yields of light olefins (ethylene and propylene). Globally, the olefin yield is at least maintained, or even improved, while at the same time eliminating the need for a steam cracking furnace dedicated to the heavy cut.

SUMMARY OF THE INVENTION

The invention relates to a process for treating a feedstock comprising a plastics pyrolysis oil, comprising:
- a) a selective hydrogenation step performed in a reaction section fed at least with said feedstock and a gas stream comprising hydrogen, in the presence of at least one selective hydrogenation catalyst, at a temperature of between 100 and 280° C., a partial pressure of hydrogen of between 1.0 and 10.0 MPa abs. and an hourly space velocity of between 0.3 and 10.0 $h^{-1}$, to obtain a hydrogenated effluent;
- b) a hydrotreatment step performed in a hydrotreatment reaction section, using at least one fixed-bed reactor containing n catalytic beds, n being an integer greater than or equal to 1, each comprising at least one hydrotreatment catalyst, said hydrotreatment reaction section being fed at least with said hydrogenated effluent obtained from step a) and a gas stream comprising hydrogen, said hydrotreatment reaction section being used at a temperature of between 250 and 430° C., a partial pressure of hydrogen of between 1.0 and 10.0 MPa abs. and an hourly space velocity of between 0.1 and 10.0 $h^{-1}$, to obtain a hydrotreatment effluent;
- c) a hydrocracking step performed in a hydrocracking reaction section, using at least one fixed-bed reactor containing n catalytic beds, n being an integer greater than or equal to 1, each comprising at least one hydrocracking catalyst, said hydrocracking reaction section being fed at least with said hydrotreated effluent obtained from step b) and a gas stream comprising hydrogen, said hydrocracking reaction section being used at a temperature of between 250 and 480° C., a partial pressure of hydrogen of between 1.5 and 25.0 MPa abs. and an hourly space velocity of between 0.1 and 10.0 $h^{-1}$, to obtain a hydrocracked effluent;
- d) a separation step, fed with the hydrocracked effluent obtained from step c) and an aqueous solution, said step being performed at a temperature of between 50 and 370° C., to obtain at least one gaseous effluent, an aqueous effluent and a hydrocarbon-based effluent.

One advantage of the process according to the invention is that of purifying an oil obtained from the pyrolysis of plastic waste of at least a part of its impurities, which makes it possible to hydrogenate it and thus to be able to upgrade it in particular by incorporating it directly into a fuel pool or else by making it compatible with a treatment in a steam cracking unit so as to be able in particular to obtain light olefins in increased yields, which may serve as monomers in the manufacture of polymers.

Another advantage of the invention is that of preventing risks of clogging and/or corrosion of the treatment unit in which the process of the invention is performed, the risks being exacerbated by the presence, often in large amounts, of diolefins, metals and halogenated compounds in the plastics pyrolysis oil.

The process of the invention thus makes it possible to obtain a hydrocarbon-based effluent obtained from a plastics pyrolysis oil which is at least partly freed of the impurities of the starting plastics pyrolysis oil, thus limiting the problems of operability, such as the corrosion, coking or catalytic deactivation problems, to which these impurities may give rise, in particular in steam cracking units and/or in units located downstream of the steam cracking units, notably the polymerization and selective hydrogenation units. The removal of at least a part of the impurities from the oils obtained from the pyrolysis of plastic waste will also make it possible to increase the range of applications of the target polymers, the application incompatibilities being reduced.

The present invention participates towards the recycling of plastics, by proposing a process for treating an oil obtained from the pyrolysis of plastics to purify it, to hydrotreat it and to hydrocrack it so as to obtain a hydrocarbon-based effluent with a reduced content of impurities which is thus upgradable, either directly in the form of a naphtha cut and/or a diesel cut, or which has a composition that is compatible with a feedstock of a steam cracking unit. Hydrocracking makes it possible to transform at least a portion of the heavy cut (diesel) into compounds of the naphtha cut, which makes it possible to obtain improved yields of naphtha cut and, when this cut is sent for steam cracking, of light olefins, while at the same time reducing, in particular, the risks of clogging during steps of treatment of plastics pyrolysis oils, such as those described in the prior art, and coke formation in large amounts and/or the corrosion risks encountered during subsequent step(s), for example during the step of steam cracking of the plastics pyrolysis oils.

According to a variant, the process also comprises a step e) of fractionating all or a portion of the hydrocarbon-based effluent obtained from step d), to obtain at least one gas stream and at least two liquid hydrocarbon-based streams, said two liquid hydrocarbon-based streams being at least one naphtha cut comprising compounds with a boiling point of less than or equal to 175° C. and one hydrocarbon cut comprising compounds with a boiling point of greater than 175° C.

According to a variant, the process also comprises a recycling step f) in which at least a fraction of the cut comprising compounds with a boiling point of greater than 175° C. obtained from the fractionation step e) is sent into the hydrocracking step c).

According to a variant, the process also comprises a recycling step g) in which a fraction of the hydrocarbon-based effluent obtained from the separation step d) or a fraction of the naphtha cut comprising compounds with a boiling point of less than or equal to 175° C. obtained from the fractionation step e) is sent into the selective hydrogenation step a) and/or the hydrotreatment step b).

According to a variant, the amount of the recycle stream from steps f) and/or g) is adjusted so that the weight ratio between the recycle stream and the feedstock comprising a plastics pyrolysis oil is less than or equal to 10.

According to a variant, a stream containing an amine is injected upstream of step a).

According to a variant, the process comprises a step a0) of pretreating the feedstock comprising a plastics pyrolysis oil, said pretreatment step being performed upstream of the selective hydrogenation step a) and comprises a filtration step and/or a step of washing with water and/or an adsorption step.

According to a variant, the reaction section of step a) or b) uses at least two reactors functioning in permutable mode.

According to a variant, said selective hydrogenation catalyst comprises a support chosen from alumina, silica, silica-aluminas, magnesia, clays and mixtures thereof and a hydro-dehydrogenating function comprising either at least one group VIII element and at least one group VIB element, or at least one group VIII element.

According to a variant, said at least one hydrotreatment catalyst comprises a support chosen from the group consisting of alumina, silica, silica-aluminas, magnesia, clays and mixtures thereof and a hydro-dehydrogenating function comprising at least one group VIII element and/or at least one group VIB element.

According to a variant, said hydrocracking catalyst comprises a support chosen from halogenated aluminas, combinations of boron and aluminium oxides, amorphous silica-aluminas and zeolites and a hydro-dehydrogenating function comprising at least one group VIB metal chosen from chromium, molybdenum and tungsten, alone or as a mixture, and/or at least one group VIII metal chosen from iron, cobalt, nickel, ruthenium, rhodium, palladium and platinum.

According to this variant, said zeolite is chosen from Y zeolites, alone or in combination, with other zeolites from among beta, ZSM-12, IZM-2, ZSM-22, ZSM-23, SAPO-11, ZSM-48 and ZBM-30 zeolites, alone or as a mixture.

According to a variant, the hydrocarbon-based effluent obtained from the separation step d), or at least one of the two liquid hydrocarbon-based streams obtained from the optional step e), is totally or partly sent into a steam cracking step h) performed in at least one pyrolysis furnace at a temperature of between 700 and 900° C. and at a pressure of between 0.05 and 0.3 MPa relative.

According to a variant, the naphtha cut comprising compounds with a boiling point of less than or equal to 175° C. obtained from step e) is fractionated into a heavy naphtha cut comprising compounds with a boiling point of between 80 and 175° C. and a light naphtha cut comprising compounds with a boiling point of less than 80° C., at least a portion of said heavy cut being sent into an aromatic complex including at least one naphtha reforming step.

According to this variant, at least a portion of the light naphtha cut is sent into the steam cracking step h).

The invention also relates to the product that may be obtained via the treatment process according to the invention.

According to the present invention, the pressures are absolute pressures, also written as abs., and are given in MPa absolute (or MPa abs.), unless otherwise indicated.

According to the present invention, the expressions "comprised between . . . and . . . " and "between . . . and . . . " are equivalent and mean that the limit values of the interval are included in the described range of values. If such were not the case and if the limit values were not included in the described range, such a clarification will be given by the present invention.

For the purposes of the present invention, the various ranges of parameters for a given step, such as the pressure ranges and the temperature ranges, may be used alone or in combination. For example, for the purposes of the present invention, a range of preferred pressure values can be combined with a range of more preferred temperature values.

In the text hereinbelow, particular and/or preferred embodiments of the invention may be described. They may be implemented separately or combined together without limitation of combination when this is technically feasible.

In the text hereinbelow, the groups of chemical elements are given according to the CAS classification (CRC Handbook of Chemistry and Physics, published by CRC Press, editor-in-chief D. R. Lide, $81^{st}$ edition, 2000-2001). For example, group VIII according to the CAS classification corresponds to the metals from columns 8, 9 and 10 according to the new IUPAC classification.

The metal content is measured by X-ray fluorescence.

DETAILED DESCRIPTION

The Feedstock

According to the invention, a "plastics pyrolysis oil" is an oil, advantageously in liquid form at room temperature, obtained from the pyrolysis of plastics, preferably of plastic waste notably originating from collection and sorting channels. It comprises in particular a mixture of hydrocarbon-based compounds, notably of paraffins, monoolefins and/or diolefins, naphthenes and aromatics, these hydrocarbon-based compounds preferably having a boiling point of less than 700° C. and preferably less than 550° C. The plastics pyrolysis oil may also comprise, and usually does comprise, impurities such as metals, notably silicon and iron, and halogenated compounds, notably chlorinated compounds. These impurities may be present in the plastics pyrolysis oil in high contents, for example up to 350 ppm by weight or even 700 ppm by weight or even 1000 ppm by weight of halogen elements provided by halogenated compounds, up to 100 ppm by weight, or even 200 ppm by weight of metallic or semi-metallic elements. Alkali metals, alkaline-earth metals, transition metals, post-transition metals and metalloids may be likened to contaminants of metallic nature, referred to as metals or metallic or semi-metallic elements. In particular, the metals or metallic or semi-metallic elements that may be contained in the oils obtained from the pyrolysis of plastic waste comprise silicon, iron or both of these elements. The plastics pyrolysis oil may also comprise other impurities such as heteroelements provided notably by sulfur compounds, oxygen compounds and/or nitrogen compounds, in contents generally less than 10 000 ppm by weight of heteroelements and preferably less than 4000 ppm by weight of heteroelements.

The feedstock of the process according to the invention comprises at least one plastics pyrolysis oil. Said feedstock may consist solely of plastics pyrolysis oil(s). Preferably, said feedstock comprises at least 50% by weight, preferably between 75% and 100% by weight, of plastics pyrolysis oil, i.e. preferably between 50% and 100% by weight and preferably between 70% and 100% by weight of plastics pyrolysis oil. The feedstock of the process according to the invention may comprise, inter alia, one or more plastics pyrolysis oils, a conventional petroleum-based feedstock or a feedstock obtained from the conversion of biomass which is then co-treated with the plastics pyrolysis oil of the feedstock.

The plastics pyrolysis oil may be obtained from a thermal, catalytic pyrolysis treatment or else may be prepared by hydropyrolysis (pyrolysis in the presence of a catalyst and of hydrogen).

Pretreatment (Optional)

Said feedstock comprising a plastics pyrolysis oil may advantageously be pretreated in an optional pretreatment step a0), prior to the selective hydrogenation step a), to obtain a pretreated feedstock which feeds step a).

This optional pretreatment step a0) makes it possible to reduce the amount of contaminants, in particular the amount of silicon, which may be present in the feedstock comprising a plastics pyrolysis oil. Thus, an optional step a0) of pretreatment of the feedstock comprising a plastics pyrolysis oil is advantageously performed in particular when said feedstock comprises more than 50 ppm by weight, notably more than 20 ppm by weight, more particularly more than 10 ppm by weight, or even more than 5 ppm by weight of metallic elements, and in particular when said feedstock comprises more than 20 ppm by weight of silicon, more particularly more than 10 ppm by weight, or even more than 5 ppm by weight and even more particularly more than 1.0 ppm by weight of silicon.

Said optional pretreatment step a0) may be performed via any method known to those skilled in the art for reducing the amount of contaminants. It may notably comprise a filtration step and/or a step of washing with water and/or an adsorption step.

According to one variant, said optional pretreatment step a0) is performed in an adsorption section operated in the presence of at least one adsorbent. Said optional pretreatment step a0) is performed at a temperature of between 0 and 150° C., preferably between 5 and 100° C., and at a pressure of between 0.15 and 10.0 MPa abs, preferably between 0.2 and 1.0 MPa abs. The adsorption section is advantageously operated in the presence of at least one adsorbent, preferably of alumina type, with a specific surface area of greater than or equal to 100 m$^2$/g, preferably greater than or equal to 200 m$^2$/g. The specific surface area of said at least one adsorbent is advantageously less than or equal to 600 m$^2$/g, in particular less than or equal to 400 m$^2$/g. The specific surface area of the adsorbent is a surface area measured by the BET method, i.e. the specific surface area determined by nitrogen adsorption in accordance with the standard ASTM D 3663-78 established from the Brunauer-Emmett-Teller method described in the periodical *The Journal of the American Chemical Society*, 60, 309 (1938).

Advantageously, said adsorbent comprises less than 1% by weight of metallic elements, and is preferably free of metallic elements. The term "metallic elements of the adsorbent" should be understood as referring to the elements from groups 6 to 10 of the Periodic Table of the Elements (new IUPAC classification).

Said adsorption section of the optional step a0) comprises at least one adsorption column, preferably comprises at least two adsorption columns, preferentially between two and four adsorption columns, containing said adsorbent. When the adsorption section comprises two adsorption columns, one operating mode may be that referred to as "swing" operating according to the dedicated terminology, in which one of the columns is on-line, i.e. in service, while the other column is in reserve. When the adsorbent of the on-line column is spent, this column is isolated, while the column in reserve is placed on-line, i.e. in service. The spent adsorbent can then be regenerated in situ and/or replaced with fresh adsorbent so that the column containing it can once again be placed on-line once the other column has been isolated.

Another operating mode is to have at least two columns operating in series. When the adsorbent of the column placed at the head is spent, this first column is isolated and the spent adsorbent is either regenerated in situ or replaced with fresh adsorbent. The column is then put back on-line in the last position, and so on. This operating mode is known as the permutable mode, or as PRS for permutable reactor system or else "lead and lag" according to the dedicated terminology. The combination of at least two adsorption columns makes it possible to overcome the possible and potentially rapid poisoning and/or clogging of the adsorbent due to the combined action of the metallic contaminants, of the diolefins, of the gums obtained from the diolefins and of the insoluble matter that may be present in the plastics pyrolysis oil to be treated. The reason for this is that the presence of at least two adsorption columns facilitates the replacement and/or regeneration of the adsorbent, advantageously without stoppage of the pretreatment unit, or even of the process, thus making it possible to reduce the risks of clogging and thus to avoid stoppage of the unit due to clogging, to control the costs and to limit the consumption of adsorbent.

Said optional pretreatment step a0) may also optionally be fed with at least a fraction of a recycle stream, advantageously obtained from step g) of the process, as a mixture with or separately from the feedstock comprising a plastics pyrolysis oil.

Said optional pretreatment step a0) thus makes it possible to obtain a pretreated feedstock which then feeds the selective hydrogenation step a).

Selective Hydrogenation Step a)

According to the invention, the process comprises a step a) of selective hydrogenation of the feedstock comprising a plastics pyrolysis oil performed in the presence of hydrogen, under hydrogen pressure and temperature conditions making it possible to maintain said feedstock in the liquid phase and with an amount of soluble hydrogen that is just necessary for selective hydrogenation of the diolefins present in the plastics pyrolysis oil. Selective hydrogenation of the diolefins in liquid phase thus makes it possible to avoid or at least to limit the formation of "gums", i.e. polymerization of the diolefins and thus the formation of oligomers and polymers, which can clog the reaction section of the hydrotreatment step b). Said selective hydrogenation step a) makes it possible to obtain a hydrogenated effluent, i.e. an effluent with a reduced content of olefins, in particular of diolefins, preferably free of diolefins.

According to the invention, said selective hydrogenation step a) is performed in a reaction section fed at least with said feedstock comprising a plastics pyrolysis oil, or with the pretreated feedstock obtained from the optional pretreatment step a0), and a gas stream comprising hydrogen ($H_2$). Optionally, the reaction section of said step a) may also be fed with at least a fraction of a recycle stream, advantageously obtained from step d) or from the optional step g), either as a mixture with said feedstock, which has optionally been pretreated, or separately from the feedstock, which has optionally been pretreated, advantageously directly at the inlet of at least one of the reactors of the reaction section of step a). The introduction of at least a fraction of said recycle stream into the reaction section of the selective hydrogenation step a) advantageously makes it possible to dilute the impurities of the feedstock, which has optionally been pretreated, and to control the temperature notably in said reaction section.

Said reaction section involves selective hydrogenation, preferably in a fixed bed, in the presence of at least one selective hydrogenation catalyst, advantageously at a temperature of between 100 and 280° C., preferably between 120 and 260° C., preferably between 130 and 250° C., a partial pressure of hydrogen of between 1.0 and 10.0 MPa abs., preferably between 1.5 and 8.0 MPa abs. and at an hourly space velocity (HSV) of between 0.3 and 10.0 h$^{-1}$, preferably between 0.5 and 5.0 h$^{-1}$. The hourly space velocity (HSV) is defined here as the ratio of the hourly volume flow rate of the feedstock comprising the plastics pyrolysis oil, which has optionally been pretreated, to the volume of catalyst(s). The amount of the gas stream comprising hydrogen ($H_2$) feeding said reaction section of step a) is advantageously such that the hydrogen coverage is between 1 and 200 $Nm^3$ of hydrogen per $m^3$ of feedstock ($Nm^3/m^3$), preferably between 1 and 50 $Nm^3$ of hydrogen per $m^3$ of feedstock ($Nm^3/m^3$), preferably between 5 and 20 $Nm^3$ of hydrogen per $m^3$ of feedstock ($Nm^3/m^3$). The hydrogen coverage is defined as the ratio of the volume flow rate of hydrogen taken under standard temperature and pressure conditions relative to the volume flow rate of "fresh" feedstock, i.e. of the feedstock to be treated, which has optionally been pretreated, without taking into account any recycled fraction, at 15° C. (in normal $m^3$, written as $Nm^3$, of $H_2$ per $m^3$ of feedstock). The gas stream comprising hydrogen, which feeds the reaction section of step a), may consist of a supply of hydrogen and/or of recycled hydrogen obtained in particular from the separation step d).

Advantageously, the reaction section of said step a) comprises between 1 and 5 reactors. According to a particular embodiment of the invention, the reaction section comprises between 2 and 5 reactors, which operate in permutable mode, referred to by the term PRS for permutable reactor system or by the term "lead and lag". Combination of at least two reactors in PRS mode makes it possible to isolate one reactor, to discharge the spent catalyst, to recharge the reactor with fresh catalyst and to return said reactor into service without stopping the process. The PRS technology is described in particular in patent FR2681871.

Advantageously, reactor inserts, for example of filter plate type, may be used to prevent the clogging of the reactor(s). An example of a filter plate is described in patent FR3051375.

Advantageously, said at least one selective hydrogenation catalyst comprises a support, preferably a mineral support, and a hydrodehydrogenating function.

According to one variant, the hydrodehydrogenating function in particular comprises at least one group VIII element, preferably chosen from nickel and cobalt, and at least one group VIB element, preferably chosen from molybdenum and tungsten. According to this variant, the total content of oxides of metallic elements from groups VIB and VIII is preferably between 1% and 40% by weight and preferentially between 5% and 30% by weight relative to the total weight of the catalyst. The weight ratio expressed as metal oxide between the group VIB metal(s) relative to the group VIII metal(s) is preferably between 1 and 20 and preferably between 2 and 10.

According to this variant, the reaction section of said step a) comprises, for example, a selective hydrogenation catalyst comprising between 0.5% and 12% by weight of nickel, preferably between 1% and 10% by weight of nickel (expressed as nickel oxide NiO relative to the weight of said catalyst), and between 1% and 30% by weight of molybdenum, preferably between 3% and 20% by weight of molybdenum (expressed as molybdenum oxide $MoO_3$ relative to the weight of said catalyst) on a support, preferably a mineral support, preferably on an alumina support.

According to another variant, the hydrodehydrogenating function comprises, and preferably consists of, at least one group VIII element, preferably nickel. According to this variant, the content of nickel oxides is preferably between 1% and 50% by weight and preferably between 10% and 30% by weight relative to the weight of said catalyst. This type of catalyst is preferably used in its reduced form, on a support which is preferably mineral, preferably on an alumina support.

The support for said at least one selective hydrogenation catalyst is preferably chosen from alumina, silica, silica-aluminas, magnesia, clays and mixtures thereof. Said support may contain other dopant compounds, notably oxides chosen from boron oxide, in particular boron trioxide, zirconia, ceria, titanium oxide, phosphorus pentoxide and a mixture of these oxides. Preferably, said at least one selective hydrogenation catalyst comprises an alumina support, optionally doped with phosphorus and optionally boron. When phosphorus pentoxide $P_2O_5$ is present, its concentration is less than 10% by weight relative to the weight of the alumina and advantageously at least 0.001% by weight relative to the total weight of the alumina. When boron trioxide $B_2O_5$ is present, its concentration is less than 10% by weight relative to the weight of the alumina and advantageously at least 0.001% by weight relative to the total weight of the alumina. The alumina used may be, for example, a γ (gamma) or η (eta) alumina.

Said selective hydrogenation catalyst is, for example, in the form of extrudates.

Very preferably, in order to hydrogenate the diolefins as selectively as possible, step a) may also use, in addition to the selective hydrogenation catalysts described above, at least one selective hydrogenation catalyst used in step a) comprising less than 1% by weight of nickel and at least 0.1% by weight of nickel, preferably 0.5% by weight of nickel, expressed as nickel oxide NiO relative to the weight of said catalyst, and less than 5% by weight of molybdenum and at least 0.1% by weight of molybdenum, preferably 0.5% by weight of molybdenum, expressed as molybdenum oxide $MoO_3$ relative to the weight of said catalyst, on an alumina support. This catalyst sparingly charged with metals is preferably placed upstream of the selective hydrogenation catalysts described above.

Optionally, the feedstock which comprises a plastics pyrolysis oil, which has optionally been pretreated, and/or optionally mixed beforehand with at least a fraction of a recycle stream, advantageously obtained from step d) or from the optional step g), may be mixed with the gas stream comprising hydrogen prior to its introduction into the reaction section.

Said feedstock, which has optionally been pretreated, and/or optionally mixed with at least a fraction of the recycle stream, advantageously obtained from step d) or from the optional step g), and/or optionally as a mixture with the gas stream, may also be heated before being introduced into the reaction section of step a), for example by heat exchange notably with the hydrotreatment effluent from step b), to reach a temperature close to the implementation temperature in the reaction section which it feeds.

The content of impurities, in particular of diolefins, of the hydrogenated effluent obtained on conclusion of step a) is reduced relative to that of the same impurities, in particular of diolefins, included in the feedstock for the process. The selective hydrogenation step a) generally makes it possible to convert at least 90% and preferably at least 99% of the diolefins contained in the initial feedstock. Step a) also makes it possible to remove, at least partly, other contaminants, for instance silicon. The hydrogenated effluent, obtained on conclusion of the selective hydrogenation step a), is sent, preferably directly, into the hydrotreatment step b). When at least a fraction of the recycle stream obtained from the optional step g) is introduced, the hydrogenated effluent obtained on conclusion of the selective hydrogenation step a) thus comprises, in addition to the converted feedstock, said fraction(s) of the recycle stream.

Hydrotreatment Step b)

According to the invention, the treatment process comprises a step b) of hydrotreatment, advantageously in a fixed bed, of said hydrogenated effluent obtained from step a), optionally as a mixture with at least a fraction of a recycle stream, advantageously obtained from step d) or from the optional steps f) and/or g), in the presence of hydrogen and of at least one hydrotreatment catalyst, to obtain a hydrotreatment effluent.

Advantageously, step b) involves the hydrotreatment reactions that are well known to those skilled in the art, and more particularly hydrogenation reactions of olefins or of aromatics, hydrodemetallation, hydrodesulfurization, hydrodeazotization, etc. reactions.

Advantageously, said step b) is performed in a hydrotreatment reaction section comprising at least one, preferably between one and five, fixed-bed reactors containing n catalytic beds, n being an integer greater than or equal to one, preferably between one and ten, preferably between two and five, said bed(s) each comprising at least one and preferably not more than ten hydrotreatment catalysts. When a reactor comprises several catalytic beds, i.e. at least two, preferably between two and ten, preferably between two and five catalytic beds, said catalytic beds are arranged in series in said reactor.

Said hydrotreatment reaction section is fed at least with said hydrogenated effluent obtained from step a) and a gas stream comprising hydrogen, advantageously into the first catalytic bed of the first functioning reactor.

Said hydrotreatment reaction section of step b) may also be fed with at least a fraction of the recycle stream, advantageously obtained from step d) or from the optional steps f) and/or g). Said fraction(s) of said recycle stream or the total amount of the recycle stream may be introduced into said hydrotreatment reaction section as a mixture with the hydrogenated effluent obtained from step a) or separately. Said fraction(s) of said recycle stream or the total amount of the recycle stream may be introduced into said hydrotreatment reaction section into one or more catalytic beds of said hydrotreatment reaction section of step b). Introduction of at least a fraction of said recycle stream advantageously makes it possible to dilute the impurities still present in the hydrogenated effluent and to control the temperature, in particular to limit the temperature increase, in the catalytic bed(s) of the hydrotreatment reaction section which involves highly exothermic reactions.

Advantageously, said hydrotreatment reaction section is implemented at a pressure equivalent to that used in the reaction section of the selective hydrogenation step a), but at a higher temperature than that of the reaction section of the selective hydrogenation step a). Thus, said hydrotreatment reaction section is advantageously implemented at a hydrotreatment temperature of between 250 and 430° C., preferably between 280 and 380° C., at a partial pressure of hydrogen of between 1.0 and 10.0 MPa abs., and at an hourly space velocity (HSV) of between 0.1 and 10.0 h$^{-1}$, preferably between 0.1 and 5.0 h$^{-1}$, preferentially between 0.2 and 2.0 h$^{-1}$, preferably between 0.2 and 0.8 h$^{-1}$. According to the invention, the "hydrotreatment temperature" corresponds to an average temperature in the hydrotreatment reaction section of step b). In particular, it corresponds to the weight-average bed temperature (WABT) according to the dedicated terminology, which is well known to those skilled in the art. The hydrotreatment temperature is advantageously determined as a function of the catalytic systems, of the equipment and of the configuration thereof that are used. For example, the hydrotreatment temperature (or WABT) is calculated in the following manner:

$$WABT=(T_{inlet}+2\times T_{outlet})/3$$

with $T_{inlet}$: the temperature of the hydrogenated effluent at the inlet of the hydrotreatment reaction section, $T_{outlet}$: the temperature of the effluent at the outlet of the hydrotreatment reaction section.

The hourly space velocity (HSV) is defined here as the ratio of the hourly volume flow rate of the hydrogenated effluent obtained from step a) per volume of catalyst(s). The hydrogen coverage in step b) is advantageously between 50 and 1000 Nm$^3$ of hydrogen per m$^3$ of fresh feedstock which feeds step a), preferably between 50 and 500 Nm$^3$ of hydrogen per m$^3$ of fresh feedstock which feeds step a), preferably between 100 and 300 Nm$^3$ of hydrogen per m$^3$ of fresh feedstock which feeds step a). The hydrogen coverage is defined here as the ratio of the volume flow rate of hydrogen taken under standard temperature and pressure conditions relative to the volume flow rate of fresh feedstock which feeds step a), i.e. of feedstock comprising a plastics pyrolysis oil, or to the feedstock which has optionally been pretreated, which feeds step a) (in normal m$^3$, written as Nm$^3$, of H$_2$ per m$^3$ of fresh feedstock). The hydrogen may consist of a supply and/or of recycled hydrogen obtained in particular from the separation step d).

Preferably, an additional gas stream comprising hydrogen is advantageously introduced into the inlet of each reactor, in particular operating in series, and/or into the inlet of each catalytic bed from the second catalytic bed of the hydrotreatment reaction section. These additional gas streams are also referred to as cooling streams. They make it possible to control the temperature in the hydrotreatment reactor in which the reactions involved are generally highly exothermic.

Advantageously, said hydrotreatment catalyst used in said step b) may be chosen from known hydrodemetallation, hydrotreatment or silicon scavenging catalysts notably used for the treatment of petroleum cuts, and combinations thereof. Known hydrodemetallation catalysts are, for example, those described in the patents EP 0113297, EP 0113284, U.S. Pat. Nos. 5,221,656, 5,827,421, 7,119,045, 5,622,616 and 5,089,463. Known hydrotreatment catalysts are, for example, those described in the patents EP 0113297, EP 0113284, U.S. Pat. No. 6,589,908, 4,818,743 or 6,332,976. Known silicon scavenging catalysts are, for example, those described in the patent applications CN 102051202 and US 2007/080099.

In particular, said hydrotreatment catalyst comprises a support, preferably a mineral support, and at least one metallic element having a hydrodehydrogenating function. Said metallic element having a hydrodehydrogenating function advantageously comprises at least one group VIII element, preferably chosen from the group consisting of nickel and cobalt, and/or at least one group VIB element, preferably chosen from the group consisting of molybdenum and tungsten. The total content of oxides of metallic elements from groups VIB and VIII is preferably between 0.1% and 40% by weight and preferentially from 5% to 35% by weight relative to the total weight of the catalyst. The weight ratio expressed as metal oxide between the group VIB metal(s) relative to the group VIII metal(s) is preferably between 1.0 and 20 and preferably between 2.0 and 10. For example, the hydrotreatment reaction section of step b) of the process comprises a hydrotreatment catalyst comprising between 0.5% and 10% by weight of nickel, preferably between 1% and 8% by weight of nickel, expressed as nickel oxide NiO relative to the total weight of the hydrotreatment catalyst, and between 1.0% and 30% by weight of molybdenum, preferably between 3.0% and 29% by weight of molybdenum, expressed as molybdenum oxide $MoO_3$ relative to the total weight of the hydrotreatment catalyst, on a mineral support.

The support for said hydrotreatment catalyst is advantageously chosen from alumina, silica, silica-aluminas, magnesia, clays and mixtures thereof. Said support may also contain other dopant compounds, notably oxides chosen from boron oxide, in particular boron trioxide, zirconia, ceria, titanium oxide, phosphorus pentoxide and a mixture of these oxides. Preferably, said hydrotreatment catalyst comprises an alumina support, preferably an alumina support doped with phosphorus and optionally boron. When phosphorus pentoxide $P_2O_5$ is present, its concentration is less than 10% by weight relative to the weight of the alumina and advantageously at least 0.001% by weight relative to the total weight of the alumina. When boron trioxide $B_2O_5$ is present, its concentration is less than 10% by weight relative to the weight of the alumina and advantageously at least 0.001% by weight relative to the total weight of the alumina. The alumina used may be, for example, a γ (gamma) or η (eta) alumina.

Said hydrotreatment catalyst is, for example, in the form of extrudates.

Advantageously, said hydrotreatment catalyst used in step b) of the process has a specific surface area of greater than or equal to 250 $m^2/g$, preferably greater than or equal to 300 $m^2/g$. The specific surface area of said hydrotreatment catalyst is advantageously less than or equal to 800 $m^2/g$, preferably less than or equal to 600 $m^2/g$, in particular less than or equal to 400 $m^2/g$. The specific surface area of the hydrotreatment catalyst is measured by the BET method, i.e. the specific surface area determined by nitrogen adsorption in accordance with the standard ASTM D 3663-78 established from the Brunauer-Emmett-Teller method described in the periodical *The Journal of the American Chemical Society*, 60, 309 (1938). Such a specific surface area makes it possible to further improve the removal of the contaminants, in particular of the metals such as silicon.

According to another aspect of the invention, the hydrotreatment catalyst as described above also comprises one or more organic compounds containing oxygen and/or nitrogen and/or sulfur. Such a catalyst is often denoted by the term "additivated catalyst". Generally, the organic compound is chosen from a compound including one or more chemical functions chosen from carboxylic, alcohol, thiol, thioether, sulfone, sulfoxide, ether, aldehyde, ketone, ester, carbonate, amine, nitrile, imide, oxime, urea and amide functions or else compounds including a furan ring or else sugars.

The hydrotreatment step b) advantageously allows optimized treatment of the hydrogenated effluent obtained from step a). It in particular makes it possible to maximize the hydrogenation of the unsaturated bonds of the olefinic compounds present in the hydrogenated effluent obtained from step a), the hydrodemetallation of said hydrogenated effluent and the scavenging of the metals, notably silicon, still present in the hydrogenated effluent. The hydrotreatment step b) also allows the hydrodeazotization (HDN) of the hydrogenated effluent, i.e. the conversion of the nitrogenous species still present in the hydrogenated effluent. Preferably, the nitrogen content of the hydrotreatment effluent obtained from step b) is less than or equal to 10 ppm by weight.

In a preferred embodiment of the invention, said hydrotreatment reaction section comprises several fixed-bed reactors, preferentially between two and five, very preferentially between two and four fixed-bed reactors, each containing n catalytic beds, n being an integer greater than or equal to one, preferably between one and ten, preferably between two and five, advantageously operating in series and/or in parallel and/or in permutable (or PRS) mode and/or in "swing" mode. The various optional operating modes, PRS (or lead and lag) mode and swing mode, are well known to those skilled in the art and are advantageously defined later. The advantage of a hydrotreatment reaction section comprising several reactors lies in optimized treatment of the hydrogenated effluent, while at the same time making it possible to reduce the risks of clogging of the catalytic bed(s) and thus to avoid stoppage of the unit due to clogging.

According to a very preferred embodiment of the invention, said hydrotreatment reaction section comprises, and preferably consists of:

(b1) two fixed-bed reactors operating in swing or permutable mode, preferably in PRS mode, each of the two reactors preferably having a catalytic bed advantageously comprising a hydrotreatment catalyst preferably chosen from known hydrodemetallation or silicon scavenging catalysts and combinations thereof, and (b2) at least one fixed-bed reactor, preferably one reactor, located downstream of the two reactors (b1), and advantageously operating in series with the two reactors (b1), said fixed-bed reactor (b2) containing between one and five catalytic beds arranged in series and each comprising between one and ten hydrotreatment catalysts, of which at least one of said hydrotreatment catalysts advantageously comprises a support and at least one metallic element preferably comprising at least one group VIII element, preferably chosen from nickel and cobalt, and/or at least one group VIB element, preferably chosen from molybdenum and tungsten.

Optionally, step b) may involve a heating section located downstream of the hydrotreatment reaction section and in which the hydrogenated effluent obtained from step a) is heated to reach a temperature suitable for the hydrotreatment, i.e. a temperature of between 250 and 430° C. Said optional heating section may thus comprise one or more exchangers, preferably allowing heat exchange between the hydrogenated effluent and the hydrotreatment effluent, and/or a preheating furnace.

Advantageously, the hydrotreatment step b) allows total hydrogenation of the olefins present in the initial feedstock and those that may be obtained after the selective hydrogenation step a), but also the at least partial conversion of other impurities present in the feedstock, such as the aromatic compounds, the metal compounds, the sulfur compounds, the nitrogen compounds, the halogen compounds (notably the chlorine compounds) and the oxygen compounds. Step b) may also make it possible to further reduce the content of contaminants, such as that of the metals, in particular the silicon content.

Hydrocracking Step c)

According to the invention, the treatment process comprises a step c) of hydrocracking, advantageously in a fixed bed, of said hydrotreated effluent obtained from step b), optionally as a mixture with at least a fraction of a recycle stream advantageously obtained from step d) or from the optional steps f) and/or g), in the presence of hydrogen and of at least one hydrocracking catalyst, to obtain a hydrocracked effluent.

Advantageously, step c) involves hydrocracking reactions that are well known to those skilled in the art, and more particularly makes it possible to convert the heavy compounds, for example compounds with a boiling point of greater than 175° C., into compounds with a boiling point of less than or equal to 175° C. contained in the hydrotreated effluent obtained from step b). Other reactions, such as the hydrogenation of olefins or of aromatics, hydrodemetallation, hydrodesulfurization, hydrodeazotization, etc. may follow.

Advantageously, said step c) is performed in a hydrocracking reaction section comprising at least one, preferably between one and five, fixed-bed reactors containing n catalytic beds, n being an integer greater than or equal to one, preferably between one and ten, preferably between two and five, said bed(s) each comprising at least one and preferably not more than ten hydrocracking catalysts. When a reactor comprises several catalytic beds, i.e. at least two, preferably between two and ten, preferably between two and five catalytic beds, said catalytic beds are arranged in series in said reactor.

The hydrotreatment step b) and the hydrocracking step c) may advantageously be performed in the same reactor or in different reactors. When they are performed in the same reactor, the reactor comprises several catalytic beds, the first catalytic beds comprising the hydrotreatment catalyst(s) and the following catalytic beds comprising the hydrocracking catalyst(s).

Said hydrocracking reaction section is fed at least with said hydrotreated effluent obtained from step b) and a gas stream comprising hydrogen, advantageously into the first catalytic bed of the first functioning reactor.

Said hydrocracking reaction section of step c) may also be fed with at least a fraction of the recycle stream advantageously obtained from step d) or from the optional steps f) and/or g). Said fraction(s) of said recycle stream or the total amount of the recycle stream may be introduced into said hydrocracking reaction section as a mixture with the hydrotreated effluent obtained from step b), or separately. Said fraction(s) of said recycle stream or the total amount of the recycle stream may be introduced into said hydrocracking reaction section into one or more catalytic beds of said hydrocracking reaction section of step c). Introduction of at least a fraction of said recycle stream advantageously makes it possible to dilute the impurities still present in the hydrogenated effluent and to control the temperature, in particular to limit the temperature increase, in the catalytic bed(s) of the hydrocracking reaction section which involves highly exothermic reactions.

Advantageously, said hydrocracking reaction section is implemented at a pressure equivalent to that used in the reaction section of the selective hydrogenation step a) or the hydrotreatment step b).

Thus, said hydrocracking reaction section is advantageously implemented at a hydrotreatment temperature of between 250 and 480° C., preferably between 320 and 450° C., at a partial pressure of hydrogen of between 1.5 and 25.0 MPa abs., preferably between 2 and 20 MPa abs., and at an hourly space velocity (HSV) of between 0.1 and 10.0 h$^{-1}$, preferably between 0.1 and 5.0 h$^{-1}$, preferentially between 0.2 and 4 h$^{-1}$. According to the invention, the "hydrocracking temperature" corresponds to an average temperature in the hydrocracking reaction section of step c). In particular, it corresponds to the weight-average bed temperature (WABT) according to the dedicated terminology, which is well known to those skilled in the art. The hydrocracking temperature is advantageously determined as a function of the catalytic systems, of the equipment and of the configuration thereof that are used. For example, the hydrocracking temperature (or WABT) is calculated in the following manner:

$$WABT=(T_{inlet}+2\times T_{outlet})/3$$

with $T_{inlet}$: the temperature of the hydrogenated effluent at the inlet of the hydrocracking reaction section, $T_{outlet}$: the temperature of the effluent at the outlet of the hydrocracking reaction section.

The hourly space velocity (HSV) is defined here as the ratio of the hourly volume flow rate of the hydrogenated effluent obtained from step a) per volume of catalyst(s). The hydrogen coverage in step c) is advantageously between 80 and 2000 Nm$^3$ of hydrogen per m$^3$ of fresh feedstock which feeds step a), preferably between 200 and 1800 Nm$^3$ of hydrogen per m$^3$ of fresh feedstock which feeds step a). The hydrogen coverage is defined here as the ratio of the volume flow rate of hydrogen taken under standard temperature and pressure conditions relative to the volume flow rate of fresh feedstock which feeds step a), i.e. of feedstock comprising a plastics pyrolysis oil, or with the feedstock which has optionally been pretreated, which feeds step a) (in normal m$^3$, written as Nm$^3$, of H$_2$ per m$^3$ of fresh feedstock). The hydrogen may consist of a supply and/or of recycled hydrogen obtained in particular from the separation step d).

Preferably, an additional gas stream comprising hydrogen is advantageously introduced into the inlet of each reactor, in particular operating in series, and/or into the inlet of each catalytic bed from the second catalytic bed of the hydrocracking reaction section. These additional gas streams are also referred to as cooling streams. They make it possible to control the temperature in the hydrocracking reactor in which the reactions involved are generally highly exothermic.

In an embodiment that makes it possible to maximize the production of a naphtha cut comprising compounds with a boiling point of less than or equal to 175° C., the operating conditions used in the hydrocracking step c) generally make it possible to obtain conversions per pass of the feedstock entering the hydrocracking step c), into products having at least 80% by volume of products with boiling points of less than or equal to 175° C., preferably less than 160° C. and preferably less than 150° C., of greater than 15% by weight and even more preferably of between 20% and 95% by weight.

The hydrocracking step c) thus does not necessarily make it possible to convert all the compounds with a boiling point of greater than 175° C. into compounds with a boiling point of less than or equal to 175° C. After the optional fractionation step e), there may thus remain a more or less substantial proportion of compounds with a boiling point of greater than 175° C. To increase the conversion, at least a portion of this unconverted cut may be recycled as described below in step f). Another portion may be purged, as described below.

In accordance with the invention, the hydrocracking step c) is performed in the presence of at least one hydrocracking catalyst.

The hydrocracking catalyst(s) used in the hydrocracking step c) are conventional hydrocracking catalysts known to those skilled in the art, of bifunctional type combining an acid function with a hydro-dehydrogenating function and optionally at least one binder matrix. The acid function is provided by supports having large surface areas (generally 150 to 800 m²/g) having surface acidity, such as halogenated (notably chlorinated or fluorinated) aluminas, combinations of boron and aluminium oxides, amorphous silica-aluminas and zeolites. The hydro-dehydrogenating function is provided by at least one metal from group VIB of the Periodic Table and/or at least one metal from group VIII.

Preferably, the hydrocracking catalyst(s) used in step c) comprise a hydro-dehydrogenating function comprising at least one metal from group VIII chosen from iron, cobalt, nickel, ruthenium, rhodium, palladium and platinum, and preferably from cobalt and nickel. Preferably, said catalyst(s) also comprise at least one metal from group VIB chosen from chromium, molybdenum and tungsten, alone or as a mixture, and preferably from molybdenum and tungsten. Hydro-dehydrogenating functions of NiMo, NiMoW or NiW type are preferred.

Preferably, the content of metal from group VIII in the hydrocracking catalyst(s) is advantageously between 0.5% and 15% by weight and preferably between 1% and 10% by weight, the percentages being expressed as weight percentage of oxides relative to the total weight of the catalyst.

Preferably, the content of metal from group VIB in the hydrocracking catalyst(s) is advantageously between 5% and 35% by weight and preferably between 10% and 30% by weight, the percentages being expressed as weight percentage of oxides relative to the total weight of the catalyst.

The hydrocracking catalyst(s) used in step c) may also optionally comprise at least one promoter element deposited on the catalyst and chosen from the group formed by phosphorus, boron and silicon, optionally at least one element from group VIIA (chlorine and fluorine preferred), optionally at least one element from group VIIB (manganese preferred), and optionally at least one element from group VB (niobium preferred).

Preferably, the hydrocracking catalyst(s) used in step c) comprise at least one amorphous or poorly crystallized porous mineral matrix of oxide type chosen from aluminas, silicas, silica-aluminas, aluminates, alumina-boron oxide, magnesia, silica-magnesia, zirconia, titanium oxide or clay, alone or as a mixture, and preferably aluminas or silica-aluminas, alone or as a mixture.

Preferably, the silica-alumina contains more than 50% by weight of alumina, preferably more than 60% by weight of alumina.

Preferably, the hydrocracking catalyst(s) used in step c) also optionally comprise a zeolite chosen from Y zeolites, preferably from USY zeolites, alone or in combination with other zeolites from among beta, ZSM-12, IZM-2, ZSM-22, ZSM-23, SAPO-11, ZSM-48 or ZBM-30 zeolites, alone or as a mixture. Preferably, the zeolite is USY zeolite alone.

When said catalyst comprises a zeolite, the content of zeolite in the hydrocracking catalyst(s) is advantageously between 0.1% and 80% by weight, preferably between 3% and 70% by weight, the percentages being expressed as percentage of zeolite relative to the total weight of the catalyst.

A preferred catalyst comprises, and preferably consists of, at least one metal from group VIB and optionally at least one non-noble metal from group VIII, at least one promoter element, and preferably phosphorus, at least one Y zeolite and at least one alumina binder.

An even more preferred catalyst comprises, and preferably consists of, nickel, molybdenum, phosphorus, a USY zeolite, and optionally also a beta zeolite, and alumina.

Another preferred catalyst comprises, and preferably consists of, nickel, tungsten, alumina and silica-alumina.

Another preferred catalyst comprises, and preferably consists of, nickel, tungsten, a USY zeolite, alumina and silica-alumina.

Said hydrocracking catalyst is, for example, in the form of extrudates.

According to another aspect of the invention, the hydrocracking catalyst as described above also comprises one or more organic compounds containing oxygen and/or nitrogen and/or sulfur. Such a catalyst is often denoted by the term "additivated catalyst". Generally, the organic compound is chosen from a compound including one or more chemical functions chosen from carboxylic, alcohol, thiol, thioether, sulfone, sulfoxide, ether, aldehyde, ketone, ester, carbonate, amine, nitrile, imide, oxime, urea and amide functions or else compounds including a furan ring or else sugars.

The preparation of the catalysts for steps a), b) or c) is known and generally comprises a step of impregnation of the group VIII metals and of the group VIB metals when present, and optionally of the phosphorus and/or boron on the support, followed by drying, and then optionally calcining. In the case of an additivated catalyst, the preparation generally takes place by simple drying without calcining after introducing the organic compound. The term "calcining" means herein a heat treatment under a gas containing air or oxygen at a temperature of greater than or equal to 200° C. Before their use in a process step, the catalysts are generally subjected to sulfurization so as to form the active species. The catalyst of step a) may also be a catalyst used in its reduced form, thus involving a reduction step in its preparation.

Optionally, step c) may involve a heating section located downstream of the hydrocracking reaction section and in which the hydrotreated effluent obtained from step b) is heated to reach a temperature suitable for the hydrocracking, i.e. a temperature of between 250 and 480° C. Said optional heating section may thus comprise one or more exchangers, preferably allowing heat exchange between the hydrotreated effluent and the hydrocracked effluent, and/or a preheating furnace.

Separation Step d)

According to the invention, the treatment process comprises a separation step d), advantageously performed in at least one washing/separation section, fed at least with the hydrocracked effluent obtained from step c) and an aqueous solution, to obtain at least one gaseous effluent, an aqueous effluent and a hydrocarbon-based effluent.

The gaseous effluent obtained on conclusion of step d) advantageously comprises hydrogen, preferably comprises at least 90% by volume, preferably at least 95% by volume, of hydrogen. Advantageously, said gaseous effluent may be at least partly recycled into the selective hydrogenation step a) and/or the hydrotreatment step b) and/or the hydrocracking step c), the recycling system possibly comprising a purification section.

The aqueous effluent obtained on conclusion of step d) advantageously comprises ammonium salts and/or hydrochloric acid.

The hydrocarbon-based effluent obtained from step d) comprises hydrocarbon-based compounds and advantageously corresponds to the plastics pyrolysis oil of the feedstock, or to the plastics pyrolysis oil and the fraction of petroleum-based feedstock or conventional biomass co-treated with the pyrolysis oil, in which at least a portion of the heavy compounds has been converted into lighter compounds so as to maximize the naphtha cut. The hydrocarbon-based effluent is also at least partly freed of its impurities, in particular of its olefinic (diolefins and monoolefins), metallic and halogenated impurities.

This separation step d) in particular makes it possible to remove the ammonium chloride salts which form by reaction between the chloride ions, released by hydrogenation of the chlorinated compounds notably in HCl form during step b) followed by dissolution in the water, and the ammonium ions, generated by hydrogenation of the nitrogenous compounds in the form of $NH_3$ notably during step b) and/or provided by injection of an amine followed by dissolution in the water, and thus to limit the risks of clogging, in particular in the transfer lines and/or in the sections of the process of the invention and/or the transfer lines to the steam cracker, due to the precipitation of the ammonium chloride salts. It also makes it possible to remove the hydrochloric acid formed by the reaction of the hydrogen ions and the chloride ions.

As a function of the content of chlorinated compounds in the initial feedstock to be treated, a stream containing an amine, for instance monoethanolamine, diethanolamine and/or monodiethanolamine, may be injected upstream of the selective hydrogenation step a), between the selective hydrogenation step a) and the hydrotreatment step b) and/or between the hydrocracking step c) and the separation step d), preferably upstream of the selective hydrogenation step a), so as to ensure a sufficient amount of ammonium ions to combine with the chloride ions formed during the hydrotreatment step, thus making it possible to limit the formation of hydrochloric acid and thus to limit corrosion downstream of the separation section.

Advantageously, the separation step d) comprises injection of an aqueous solution, preferably injection of water, into the hydrocracked effluent obtained from step c), upstream of the washing/separation section, so as to at least partly dissolve the ammonium chloride salts and/or the hydrochloric acid and thus to improve the removal of the chlorinated impurities and to reduce the risks of clogging caused by accumulation of the ammonium chloride salts.

The separation step d) is advantageously performed at a temperature of between 50 and 370° C., preferentially between 100 and 340° C., preferably between 200 and 300° C. Advantageously, the separation step d) is performed at a pressure close to that used in steps a) and/or b) and/or c), preferably between 1.0 and 10.0 MPa, so as to facilitate the recycling of hydrogen.

The washing/separation section of step d) may be at least partly performed in common or separate washing and separation equipment, this equipment being well known (separating vessels which may be operated at various pressures and temperatures, pumps, heat exchangers, washing columns, etc.).

In an optional embodiment of the invention, taken in addition with or separately from other described embodiments of the invention, the separation step d) comprises the injection of an aqueous solution into the hydrocracked effluent obtained from step c), followed by the washing/separation section advantageously comprising a separation phase for obtaining at least one aqueous effluent charged with ammonium salts, a washed liquid hydrocarbon-based effluent and a partially washed gaseous effluent. The aqueous effluent charged with ammonium salts and the washed liquid hydrocarbon-based effluent may subsequently be separated in a decanting vessel so as to obtain said hydrocarbon-based effluent and said aqueous effluent. Said partially washed gaseous effluent may, in parallel, be introduced into a washing column where it circulates counter-currentwise relative to an aqueous stream, preferably of the same nature as the aqueous solution injected into the hydrocracked effluent, which makes it possible to at least partly, and preferably totally, remove the hydrochloric acid contained in the partially washed gaseous effluent and thus to obtain said gaseous effluent, preferably essentially comprising hydrogen, and an acidic aqueous stream. Said aqueous effluent obtained from the decanting vessel may optionally be mixed with said acidic aqueous stream, and be used, optionally as a mixture with said acidic aqueous stream, in a water recycling circuit to feed step d) of separation into said aqueous solution upstream of the washing/separation section and/or into said aqueous stream in the washing column. Said water recycling circuit may include a supply of water and/or of a basic solution and/or a purge for removing the dissolved salts.

In another optional embodiment of the invention, taken separately or in combination with other described embodiments of the invention, the separation step d) may advantageously comprise a "high-pressure" washing/separation section which operates at a pressure close to the pressure of the selective hydrogenation step a) and/or of the hydrotreatment step b) and/or of the hydrocracking step c), so as to facilitate the recycling of hydrogen. This optional "high-pressure" section of step d) may be completed with a "low-pressure" section, so as to obtain a hydrocarbon-based liquid fraction free of a portion of the gases dissolved at high pressure and intended to be treated directly in a steam cracking process or optionally to be sent into the fractionation step e).

The gas fraction(s) obtained from the separation step d) may undergo additional purification(s) and separation(s) for the purpose of recovering at least one hydrogen-rich gas which may be recycled upstream of steps a) and/or b) and/or c) and/or light hydrocarbons, notably ethane, propane and butane, which may advantageously be sent separately or as a mixture into one or more furnaces of the steam cracking step h) so as to increase the overall yield of olefins.

The hydrocarbon-based effluent obtained from the separation step d) is sent, partly or totally, either directly to the inlet of a steam cracking unit, or into an optional fractionation step e). Preferably, the hydrocarbon-based liquid effluent is sent, partly or totally, preferably totally, into a fractionation step e).

Fractionation Step e) (Optional)

The process according to the invention may comprise a step of fractionating all or a portion, preferably all, of the hydrocarbon-based effluent obtained from step d), to obtain at least one gas stream and at least two liquid hydrocarbon-based streams, said two liquid hydrocarbon-based streams being at least one naphtha cut comprising compounds with a boiling point of less than or equal to 175° C., in particular between 80 and 175° C., and one hydrocarbon cut comprising compounds with a boiling point of greater than 175° C.

Step e) makes it possible in particular to remove the gases dissolved in the hydrocarbon-based liquid effluent, for instance ammonia, hydrogen sulfide and light hydrocarbons containing 1 to 4 carbon atoms.

The optional fractionation step e) is advantageously performed at a pressure of less than or equal to 1.0 MPa abs., preferably between 0.1 and 1.0 MPa abs.

According to one embodiment, step e) may be performed in a section advantageously comprising at least one stripping column equipped with a reflux circuit comprising a reflux vessel. Said stripping column is fed with the hydrocarbon-based liquid effluent obtained from step d) and with a steam stream. The hydrocarbon-based liquid effluent obtained from step d) may optionally be heated before entering the stripping column. Thus, the lightest compounds are entrained the top of the column and into the reflux circuit comprising a reflux vessel in which a gas/liquid separation is performed. The gaseous phase which comprises the light hydrocarbons is withdrawn from the reflux vessel as a gas stream. The naphtha cut comprising compounds with a boiling point of less than or equal to 175° C. is advantageously withdrawn from the reflux vessel. The hydrocarbon cut comprising compounds with a boiling point of greater than 175° C. is advantageously withdrawn at the bottom of the stripping column.

According to other embodiments, the fractionation step e) may involve a stripping column followed by distillation column or only a distillation column.

The naphtha cut comprising compounds with a boiling point of less than or equal to 175° C. and the cut comprising compounds with a boiling point of greater than 175° C., which are optionally mixed, may be sent, totally or partly, to a steam cracking unit, at the outlet of which olefins may be (re)formed to participate in the formation of polymers. Preferably, only a portion of said cuts is sent to a steam cracking unit; at least a fraction of the remaining portion is optionally sent into the recycling step f) or g) and/or into a fuel pool, for example a naphtha pool, a diesel pool or a kerosene pool, obtained from conventional petroleum-based feedstocks.

According to a preferred embodiment, the naphtha cut comprising compounds with a boiling point of less than or equal to 175° C. is sent, totally or partly, to a steam cracking unit, whereas the cut comprising compounds with a boiling point of greater than 175° C. is sent into the recycling step f) and/or to a fuel pool.

In a particular embodiment, the optional fractionation step e) may make it possible to obtain, besides a gas stream, a naphtha cut comprising compounds with a boiling point of less than or equal to 175° C., preferably between 80 and 175° C., and a middle distillate cut comprising compounds with a boiling point of greater than 175° C. and less than 385° C., and a hydrocarbon cut comprising compounds with a boiling point of greater than or equal to 385° C., known as the heavy hydrocarbon cut. The naphtha cut may be sent, totally or partly, to a steam cracking unit and/or to the naphtha pool obtained from conventional petroleum-based feedstocks; it may also be sent into the recycling step g); the diesel cut may also be sent, totally or partly, either to a steam cracking unit, or to a diesel pool obtained from conventional petroleum-based feedstocks, or sent into the recycling step f); the heavy cut may, for its part, be sent, at least partly, to a steam cracking unit, or may be sent into the recycling step f).

In another particular embodiment, the optional fractionation step e) may make it possible to obtain, besides a gas stream, a naphtha cut comprising compounds with a boiling point of less than or equal to 175° C., preferably between 80 and 175° C., and a kerosene cut comprising compounds with a boiling point of greater than 175° C. and less than 280° C., and a diesel cut comprising compounds with a boiling point of greater than 280° C. and less than 385° C., and a hydrocarbon cut comprising compounds with a boiling point of greater than or equal to 385° C., known as the heavy hydrocarbon cut. The naphtha cut may be sent, totally or partly, to a steam cracking unit and/or to the naphtha pool obtained from conventional petroleum-based feedstocks; it may also be sent into the recycling step g); the kerosene or diesel cut may also be sent, totally or partly, either to a steam cracking unit, or to a kerosene or diesel pool respectively obtained from conventional petroleum-based feedstocks, or sent into the recycling step f); the heavy cut may, for its part, be sent, at least partly, to a steam cracking unit, or may be sent into the recycling step f).

In another particular embodiment, the naphtha cut comprising compounds with a boiling point of less than or equal to 175° C. obtained from step e) is fractionated into a heavy naphtha cut comprising compounds with a boiling point of between 80 and 175° C. and a light naphtha cut comprising compounds with a boiling point of less than 80° C., at least a portion of said heavy naphtha cut being sent into an aromatic complex including at least one naphtha reforming step for the purpose of producing aromatic compounds. According to this embodiment, at least a portion of the light naphtha cut is sent into the steam cracking step h) described below.

The gas fraction(s) obtained from the fractionation step e) may undergo additional purification(s) and separation(s) for the purpose of recovering at least light hydrocarbons, notably ethane, propane and butane, which may advantageously be sent separately or as a mixture into one of the furnaces of the steam cracking step h) so as to increase the overall yield of olefins.

Step f) (Optional) of Recycling of the Cut Comprising Compounds with a Boiling Point of Greater than 175° C.

The process according to the invention may comprise the recycling step f), in which at least a fraction of the cut comprising compounds with a boiling point of greater than 175° C. obtained from the fractionation step e) is recovered to constitute a recycle stream which is sent upstream of or directly into at least one of the reaction steps of the process according to the invention, in particular into the selective hydrogenation step a) and/or the hydrotreatment step b) and/or the hydrocracking step c). Optionally, a fraction of the recycle stream may be sent into the optional step a0).

The recycle stream may feed said reaction steps a) and/or b) and/or c) in a single injection or may be divided into several fractions to feed the reaction steps a) and/or b) and/or c) in several injections, i.e. into different catalytic beds.

Advantageously, the amount of the recycle stream of the cut comprising compounds with a boiling point of greater than 175° C. is adjusted so that the weight ratio between the recycle stream and the feedstock comprising a plastics pyrolysis oil, i.e. the feedstock to be treated feeding the overall process, is less than or equal to 10, preferably less than or equal to 5, and preferentially greater than or equal to 0.001, preferably greater than or equal to 0.01, and preferably greater than or equal to 0.1. Very preferably, the amount of the recycle stream is adjusted so that the weight ratio between the recycle stream and the feedstock comprising a plastics pyrolysis oil is between 0.2 and 5.

Preferably, the process according to the invention comprises the recycling step f). Very preferably, at least a fraction of the cut comprising compounds with a boiling point of greater than 175° C. obtained from the fractionation step e) is sent into the hydrocracking step c). The recycling of a portion of the cut comprising compounds with a boiling point of greater than 175° C. into or upstream of at least one of the reaction steps of the process according to the invention, and notably into the hydrocracking step c), advantageously makes it possible to increase the yield of naphtha cut with a boiling point of less than 175° C. The recycling also makes it possible to dilute the impurities and moreover to control the temperature in the reaction step(s) in which the reactions involved may be highly exothermic.

A purge may be installed on the recycling of said cut comprising compounds with a boiling point of greater than 175° C. Depending on the operating conditions of the process, said purge may be between 0 and 10% by weight of the cut comprising compounds with a boiling point of greater than 175° C. relative to the entering feedstock, and preferably between 0.5% and 5% by weight.

Step g) (Optional) of Recycling of the Hydrocarbon-Based Effluent Obtained from Step d) and/or of the Naphtha Cut with a Boiling Point of Less than or Equal to 175° C. Obtained from Step e)

The process according to the invention may comprise the recycling step g), in which a fraction of the hydrocarbon-based effluent obtained from the separation step d) or a fraction of the naphtha cut with a boiling point of less than or equal to 175° C. obtained from the optional fractionation step e) is recovered to constitute a recycle stream which is sent upstream of or directly into at least one of the reaction steps of the process according to the invention, in particular into the selective hydrogenation step a) and/or the hydrotreatment step b). Optionally, a fraction of the recycle stream may be sent into the optional pretreatment step a0). Preferably, the process according to the invention comprises the recycling step g).

Preferably, at least a fraction of the hydrocarbon-based effluent obtained from the separation step d) or of the naphtha cut with a boiling point of less than or equal to 175° C. obtained from the optional fractionation step e) feeds the hydrotreatment step b).

Advantageously, the amount of the recycle stream, i.e. the fraction of recycled product obtained, is adjusted so that the weight ratio between the recycle stream and the feedstock comprising a plastics pyrolysis oil, i.e. the feedstock to be treated feeding the overall process, is less than or equal to 10, preferably less than or equal to 5, and preferentially greater than or equal to 0.001, preferably greater than or equal to 0.01, and preferably greater than or equal to 0.1. Very preferably, the amount of the recycle stream is adjusted so that the weight ratio between the recycle stream and the feedstock comprising a plastics pyrolysis oil is between 0.2 and 5.

Advantageously, for the starting phases of the process, a hydrocarbon cut external to the process may be used as recycle stream. A person skilled in the art will then know how to choose said hydrocarbon cut.

The recycling of a portion of the product obtained into or upstream of at least one of the reaction steps of the process according to the invention advantageously makes it possible, firstly, to dilute the impurities and, secondly, to control the temperature in the reaction step(s) in which the reactions involved may be highly exothermic.

According to a preferred embodiment of the invention, the process for treating a feedstock comprising a plastics pyrolysis oil comprises, and preferably consists of, the sequence of steps, preferably in the given order, a) of selective hydrogenation, b) of hydrotreatment, c) of hydrocracking, d) of separation and e) of fractionation, to produce an effluent, at least a portion of which is compatible for treatment in a steam cracking unit.

According to another preferred embodiment of the invention, the process for treating a feedstock comprising a plastics pyrolysis oil comprises, and preferably consists of, the sequence of steps, preferably in the given order, a0) of pretreatment, a) of selective hydrogenation, b) of hydrotreatment, c) of hydrocracking, d) of separation and e) of fractionation, to produce an effluent, at least a portion of which is compatible for treatment in a steam cracking unit.

According to a third preferred embodiment of the invention, the process for treating a feedstock comprising a plastics pyrolysis oil comprises, and preferably consists of, the sequence of steps, preferably in the given order, a) of selective hydrogenation, b) of hydrotreatment, c) of hydrocracking, d) of separation, e) of fractionation and f) of recycling of the cut comprising compounds with a boiling point of greater than 175° C., to produce an effluent, at least a portion of which is compatible for treatment in a steam cracking unit.

According to a fourth preferred embodiment of the invention, the process for treating a feedstock comprising a plastics pyrolysis oil comprises, and preferably consists of, the sequence of steps, preferably in the given order, a0) of pretreatment, a) of selective hydrogenation, b) of hydrotreatment, c) of hydrocracking, d) of separation, e) of fractionation and f) of recycling of the cut comprising compounds with a boiling point of greater than 175° C., to produce an effluent, at least a portion of which is compatible for treatment in a steam cracking unit.

According to a fifth preferred embodiment of the invention, the process for treating a feedstock comprising a plastics pyrolysis oil comprises, and preferably consists of, the sequence of steps, preferably in the given order, a) of selective hydrogenation, b) of hydrotreatment, c) of hydrocracking, d) of separation, e) of fractionation, f) of recycling of the cut comprising compounds with a boiling point of greater than 175° C. and g) of recycling of the cut comprising compounds with a boiling point of less than or equal to 175° C., to produce an effluent, at least a portion of which is compatible for treatment in a steam cracking unit.

According to a sixth preferred embodiment of the invention, the process for treating a feedstock comprising a plastics pyrolysis oil comprises, and preferably consists of, the sequence of steps, preferably in the given order, a0) of pretreatment, a) of selective hydrogenation, b) of hydrotreatment, c) of hydrocracking, d) of separation, e) of fractionation, f) of recycling of the cut comprising compounds with a boiling point of greater than 175° C. and g) of recycling of the cut comprising compounds with a boiling point of less than or equal to 175° C., to produce an effluent, at least a portion of which is compatible for treatment in a steam cracking unit.

According to a seventh very preferred embodiment of the invention, the process for treating a feedstock comprising a plastics pyrolysis oil comprises, and preferably consists of, the sequence of steps, preferably in the given order, a0) of pretreatment, a) of selective hydrogenation, b) of hydrotreatment, c) of hydrocracking, d) of separation, e) of fractionation, f) of recycling of the cut comprising compounds with a boiling point of greater than 175° C. into step c), and g) of recycling of the cut comprising compounds with a boiling point of less than or equal to 175° C. into steps a) and/or b), to produce an effluent, at least a portion of which is compatible for treatment in a steam cracking unit.

Said hydrocarbon-based effluent or said hydrocarbon-based stream(s) thus obtained by treatment according to the process of the invention of a plastics pyrolysis oil has (have) a composition that is compatible with the specifications for a feedstock entering a steam cracking unit. In particular, the composition of the hydrocarbon-based effluent or of said hydrocarbon-based stream(s) is preferably such that:

the total content of metallic elements is less than or equal to 5.0 ppm by weight, preferably less than or equal to 2.0 ppm by weight, preferentially less than or equal to 1.0 ppm by weight and preferably less than or equal to 0.5 ppm by weight, with:

a content of silicon element (Si) of less than or equal to 1.0 ppm, preferably less than or equal to 0.6 ppm by weight, and a content of iron element (Fe) of less than or equal to 100 ppb by weight, the sulfur content is less than or equal to 500 ppm by weight, preferably less than or equal to 200 ppm by weight, the nitrogen content is less than or equal to 100 ppm by weight, preferably less than or equal to 50 ppm by weight and preferably less than or equal to 5 ppm by weight, the content of asphaltenes is less than 5.0 ppm by weight, the total content of chlorine element is less than or equal to 10 ppm by weight, preferably less than 1.0 ppm by weight, the content of olefinic compounds (monoolefins and diolefins) is less than or equal to 5.0% by weight, preferably less than or equal to 2.0% by weight and preferably less than or equal to 0.1% by weight.

The contents are given as relative weight concentrations, weight percentages (%), parts per million (ppm) by weight or parts per billion (ppb) by weight, relative to the total weight of the stream under consideration.

The process according to the invention thus make it possible to treat the plastics pyrolysis oils to obtain an effluent which can be totally or partly injected into a steam cracking unit.

Step h) of Steam Cracking (Optional)

The hydrocarbon-based effluent obtained from the separation step d), or at least one of the two liquid hydrocarbon-based streams obtained from the optional step e), may be totally or partly sent into a steam cracking step h).

Advantageously, the gas fraction(s) obtained from the separation step d) and/or the fractionation step e) and containing ethane, propane and butane, may also be totally or partly sent into the steam cracking step h).

Said steam cracking step h) is advantageously performed in at least one pyrolysis furnace at a temperature of between 700 and 900° C., preferably between 750 and 850° C., and under a pressure of between 0.05 and 0.3 MPa relative. The residence time of the hydrocarbon-based compounds is generally less than or equal to 1.0 second (noted as s), preferably between 0.1 and 0.5 s. Steam is advantageously introduced upstream of the optional steam cracking step h) and after the separation (or fractionation). The amount of water introduced, advantageously in the form of steam, is advantageously between 0.3 and 3.0 kg of water per kg of hydrocarbon-based compounds entering step h). The optional step h) is preferably performed in a plurality of pyrolysis furnaces in parallel, so as to adapt the operating conditions to the various streams feeding step h) and notably obtained from step e), and also to manage the tube decoking times. A furnace comprises one or more tubes arranged in parallel. A furnace may also denote a group of furnaces operating in parallel. For example, a furnace may be dedicated to the cracking of the naphtha cut comprising compounds with a boiling point of less than or equal to 175° C.

The effluents from the various steam cracking furnaces are generally recombined before separation so as to constitute an effluent. It is understood that the steam cracking step h) includes the steam cracking furnaces but also the substeps associated with steam cracking that are well known to those skilled in the art. These substeps may notably include heat exchangers, columns and catalytic reactors and recycling into the furnaces. A column generally makes it possible to fractionate the effluent for the purpose of recovering at least one light fraction comprising hydrogen and compounds containing 2 to 5 carbon atoms, and a fraction comprising pyrolysis gasoline, and optionally a fraction comprising pyrolysis oil. Columns make it possible to separate the various constituents of the fractionation light fraction so as to recover at least one cut rich in ethylene (C2 cut) and a cut rich in propylene (C3 cut) and optionally a cut rich in butenes (C4 cut). The catalytic reactors notably make it possible to perform selective hydrogenations of the C2, C3 or even C4 cuts and of the pyrolysis gasoline. The saturated compounds, notably the saturated compounds containing 2 to 4 carbon atoms, are advantageously recycled into the steam cracking furnaces so as to increase the overall yields of olefins.

This steam cracking step h) makes it possible to obtain at least one effluent containing olefins comprising 2, 3 and/or 4 carbon atoms (i.e. C2, C3 and/or C4 olefins), in satisfactory contents, in particular greater than or equal to 30% by weight, notably greater than or equal to 40% by weight, or even greater than or equal to 50% by weight of total olefins comprising 2, 3 and 4 carbon atoms relative to the weight of the steam cracking effluent under consideration. Said C2, C3 and C4 olefins may then be advantageously used as polyolefin monomers.

According to one or more preferred embodiments of the invention, taken separately or combined, the process for treating a feedstock comprising a plastics pyrolysis oil comprises, and preferably consists of, the sequence of steps described above, preferably in the given order, i.e.: a) of selective hydrogenation, b) of hydrotreatment, c) of hydrocracking, d) of separation and step h) of steam cracking.

According to a preferred embodiment, the process for treating a feedstock comprising a plastics pyrolysis oil comprises, and preferably consists of, the sequence of steps described above, preferably in the given order, i.e. a0) of pretreatment, a) of selective hydrogenation, b) of hydrotreatment, c) of hydrocracking, d) of separation, e) of fractionation, f) of recycling of the cut comprising compounds with a boiling point of greater than 175° C. into step c), g) of recycling of the naphtha cut comprising compounds with a boiling point of less than or equal to 175° C. into steps a) and/or b), and step h) of steam cracking.

The process according to the invention, when it comprises this steam cracking step h), thus makes it possible to obtain from plastics pyrolysis oils, for example plastic waste, olefins that can serve as monomers for the synthesis of new polymers contained in plastics, in relatively satisfactory yields, without clogging or corrosion of the units.

Analysis Methods Used

The analysis methods and/or standards used for determining the characteristics of the various streams, in particular of the feedstock to be treated and of the effluents, are known to those skilled in the art. They are in particular listed below:

TABLE 1

| Characteristics | Methods |
| --- | --- |
| Density at 15° C. | ASTM D4052 |
| Sulfur content | ISO 20846 |

TABLE 1-continued

| Characteristics | Methods |
|---|---|
| Nitrogen content | ASTM D4629 |
| Acid number | ASTM D664 |
| Bromine content | ASTM D1159 |
| Content of diolefins from the maleic anhydride number | MAV method as described in the article: C. López-García et al., Near Infrared Monitoring of Low Conjugated Diolefins Content in Hydrotreated FCC Gasoline Streams, Oil & Gas Science and Technology - Rev. IFP, volume 62 (2007), No. 1, 57-68 |
| Content of oxygen compounds | Combustion + infrared |
| Content of paraffins | UOP990-11 |
| Content of naphthenes | UOP990-11 |
| Content of olefins | UOP990-11 |
| Content of aromatics | UOP990-11 |
| Content of halogens | ASTM-D7359 |
| Content of asphaltenes | IFP9313 |
| Chloride content | ASTM D7536 |
| Content of metals: | ASTM-D5185 |
| P | |
| Fe | |
| Si | |
| Na | |
| B | |
| Simulated distillation | ASTM D2887 |

BRIEF DESCRIPTION OF THE DRAWINGS

The information regarding the elements referenced in FIGS. 1 to 4 enables a better understanding of the invention, without said invention being limited to the particular embodiments illustrated in FIGS. 1 to 4. The various embodiments presented may be used alone or in combination with each other, without any limit to the combinations.

Instead of injecting the amine stream 3 into the inlet of the selective hydrogenation step a), it is possible to inject it into the inlet of the hydrotreatment step b), into the inlet of the hydrocracking step c), into the inlet of the separation step d) or else not to inject it, depending on the characteristics of the feedstock.

Figure 1:
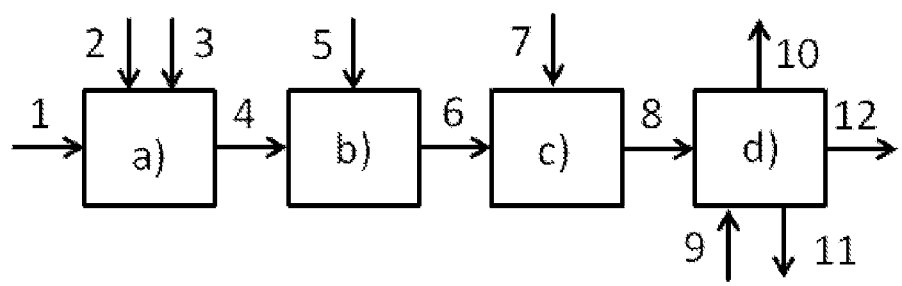
FIG. 1 represents the scheme of a particular embodiment of the process of the present invention, comprising:
- a step a) of selective hydrogenation of a hydrocarbon-based feedstock obtained from the pyrolysis of plastics 1, in the presence of a hydrogen-rich gas 2 and optionally of an amine supplied by the stream 3, performed in at least one fixed-bed reactor including at least one selective hydrogenation catalyst, to obtain an effluent 4;
- a step b) of hydrotreatment of the effluent 4 obtained from step a), in the presence of hydrogen 5, performed in at least one fixed-bed reactor including at least one hydrotreatment catalyst, to obtain a hydrotreated effluent 6;
- a step c) of hydrocracking of the effluent 6 obtained from step c), in the presence of hydrogen 7, performed in at least one fixed-bed reactor including at least one hydrocracking catalyst, to obtain a hydrocracked effluent 8;
- a step d) of separation of the effluent 8 performed in the presence of an aqueous washing solution 9, making it possible to obtain at least one fraction 10 comprising hydrogen, an aqueous fraction 11 containing dissolved salts, and a hydrocarbon-based liquid fraction 12.
Figure 2:
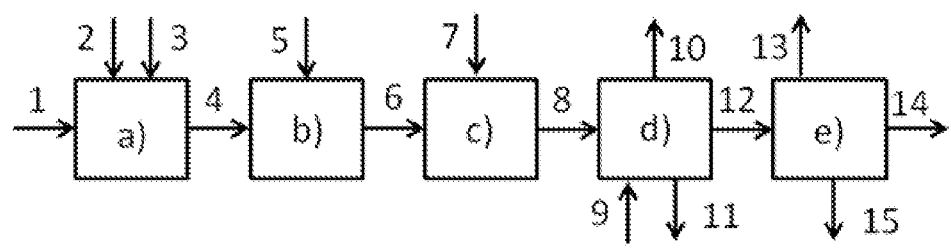

FIG. 2 represents another particular embodiment of the process according to the invention. In the embodiment shown in FIG. 2, the hydrocarbon-based liquid fraction 12, obtained on conclusion of step d), is sent into a fractionation step e) making it possible to obtain at least one gas fraction 13, a naphtha cut 14 comprising compounds with a boiling point of less than or equal to 175° C. and a cut 15 comprising compounds with a boiling point of greater than 175° C. On conclusion of step e), the naphtha cut 14 comprising compounds with a boiling point of less than or equal to 175° C. is sent into a steam cracking process (not shown).

Figure 3:
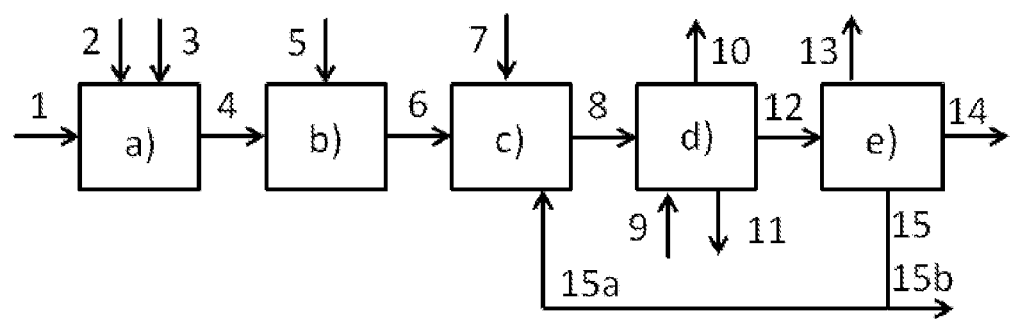

FIG. 3 represents another particular embodiment of the process according to the invention. In the embodiment shown in FIG. 3, a portion 15a of the cut 15 comprising compounds with a boiling point of greater than or equal to 175° C. obtained from step e) constitutes the recycle stream which feeds the hydrocracking step c). Another portion 15b constitutes the purge.

Figure 4:
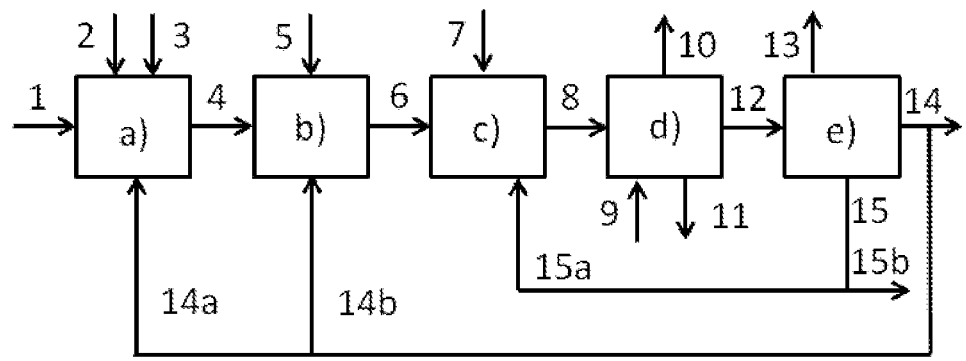

FIG. 4 represents another particular embodiment of the process according to the invention. In the embodiment shown in FIG. 4, a portion of the naphtha cut 14 comprising compounds with a boiling point of less than or equal to 175° C. obtained from step e) constitutes the recycle stream which feeds the selective hydrogenation step a) (fraction 14a), and the hydrotreatment step b) (fraction 14b).

Only the main steps, with the main streams, are shown in FIGS. 1 to 4, so as to allow a better understanding of the invention. It is clearly understood that all the equipment required for the functioning is present (vessels, pumps, exchangers, furnaces, columns, etc.), even if it is not shown. It is also understood that hydrogen-rich gas streams (supply or recycle), as described above, may be injected into the inlet of each reactor or catalytic bed or between two reactors or two catalytic beds. Means well known to those skilled in the art for purifying and recycling hydrogen may also be used.

EXAMPLES

Example 1 (in Accordance with the Invention)

The feedstock 1 treated in the process is a plastics pyrolysis oil (i.e. comprising 100% by weight of said plastics pyrolysis oil) having the characteristics indicated in Table 2.

TABLE 2

| feedstock characteristics | | | |
|---|---|---|---|
| Description/ | Methods | Unit | Pyrolysis oil |
| Density at 15° C. | ASTM D4052 | g/cm³ | 0.820 |
| Sulfur content | ISO 20846 | ppm by weight | 2500 |
| Nitrogen content | ASTM D4629 | ppm by weight | 730 |
| Acid number | ASTM D664 | mg KOH/g | 1.5 |
| Bromine content | ASTM D1159 | g/100 g | 80 |
| Content of diolefins from the maleic anhydride number | MAV method[1] | Weight % | 10 |
| Content of oxygen compounds | Combustion + infrared | Weight % | 1.0 |
| Content of paraffins | U0P990-11 | Weight % | 45 |
| Content of naphthenes | U0P990-11 | Weight % | 20 |
| Content of olefins | U0P990-11 | Weight % | 25 |
| Content of aromatics | U0P990-11 | Weight % | 10 |
| Content of halogens | ASTM-D7359 | ppm by weight | 350 |
| Content of asphaltenes | IFP9313 | ppm by weight | 380 |
| Chloride content | ASTM D7536 | ppm by weight | 320 |
| Content of metals: | | | |
| P | ASTM-D5185 | ppm by weight | 10 |
| Fe | | ppm by weight | 25 |
| Si | | ppm by weight | 45 |
| Na | | ppm by weight | 2 |
| B | | ppm by weight | 2 |
| Simulated distillation: | | | |
| 0% | ASTM D2887 | ° C. | 40 |
| 10% | | ° C. | 98 |
| 30% | | ° C. | 161 |
| 50% | | ° C. | 232 |
| 70% | | ° C. | 309 |
| 90% | | ° C. | 394 |
| 100% | | ° C. | 432 |

[1]MAV method described in the article: C. López-García et al., Near Infrared Monitoring of Low Conjugated Diolefins Content in Hydrotreated FCC Gasoline Streams, Oil & Gas Science and Technology - Rev. IFP, Vol. 62 (2007), No. 1, pages 57-68

The feedstock 1 is subjected to a selective hydrogenation step performed a) in a fixed-bed reactor and in the presence of hydrogen 2 and of a selective hydrogenation catalyst of NiMo type on alumina, under the conditions indicated in Table 3.

TABLE 3

| conditions of the selective hydrogenation step a) | | |
|---|---|---|
| Temperature | ° C. | 180 |
| Partial pressure of hydrogen | MPa abs | 6.4 |
| H₂/HC (volume coverage of hydrogen relative to the feedstock volume) | Nm³/m³ | 50 |
| HSV (volume flow rate of feedstock/ volume of catalysts) | h⁻¹ | 0.5 |

On conclusion of the selective hydrogenation step a), all of the diolefins initially present in the feedstock were converted.

The effluent 4 obtained from the selective hydrogenation step a) is subjected directly, without separation, to a hydrotreatment step b) performed in a fixed bed in the presence of hydrogen 5 and of a hydrotreatment catalyst of NiMo type on alumina under the conditions presented in Table 4.

TABLE 4

| conditions of the hydrotreatment step b) | | |
|---|---|---|
| Hydrotreatment temperature | ° C. | 355 |
| Partial pressure of hydrogen | MPa abs | 6.2 |

TABLE 4-continued

| conditions of the hydrotreatment step b) | | |
|---|---|---|
| H₂/HC (volume coverage of hydrogen relative to the feedstock volume) | Nm³/m³ | 300 |
| HSV (volume flow rate of feedstock/ volume of catalysts) | h⁻¹ | 0.5 |

The effluent 6 obtained from the hydrotreatment step b) is subjected directly, without separation, to a hydrocracking step c) performed in a fixed bed in the presence of hydrogen 7 and of a zeolitic hydrocracking catalyst comprising NiMo under the conditions presented in Table 5.

TABLE 5

| conditions of the hydrocracking step c) | | |
|---|---|---|
| Hydrocracking temperature | ° C. | 350 |
| Partial pressure of hydrogen | MPa abs | 5.8 |
| H₂/HC (volume coverage of hydrogen relative to the feedstock volume) | Nm³/m³ | 350 |
| HSV (volume flow rate of feedstock/ volume of catalysts) | h⁻¹ | 2 |

The effluent 8 obtained from the hydrocracking step c) is subjected to a separation step d) according to the invention in which a stream of water 9 is injected into the effluent obtained from the hydrocracking step c); the mixture is then sent into the separation step d) and is treated in a column for washing the acidic gases. A gas fraction 10 is obtained at the top of the acidic gas washing column whereas, at the bottom, a two-phase separating vessel makes it possible to separate an aqueous phase and a liquid phase. The gas washing column and the two-phase separator are operated at high pressure. The liquid phase is then sent into a low-pressure vessel so as to recover a second gas fraction, which is purged, and a liquid effluent. The yields for the various products and for the various fractions obtained at the outlet of the hydrocracking step c) are indicated in Table 6 (the yields corresponding to the ratios of the mass amounts of the various products obtained relative to the mass of feedstock upstream of step a), expressed in percentages and noted as % m/m).

TABLE 6 yields for the various products and fractions obtained at the outlet of the hydrocracking step c)

| | | |
|---|---|---|
| $H_2S$ | % m/m | 0.27 |
| $NH_3$ | % m/m | 0.09 |
| C1 | % m/m | 0.17 |
| C2 | % m/m | 0.26 |
| C3 | % m/m | 1.65 |
| C4 | % m/m | 7.01 |
| PI+ Fraction | | 92.69 |
| Total | % m/m | 102.14 |

The characteristics of the PI+ fraction (which corresponds to the liquid effluent 12) obtained after the separation step d) are presented in Table 7:

TABLE 7 characteristics of the PI+ fraction

| | | PI+ Fraction |
|---|---|---|
| Density at 15° C. (ASTM D4052) | g/cm³ | 0.759 |
| Content of: | | |
| Sulfur (ASTM D5453) | ppm by weight | <2 |
| Nitrogen (ASTM D4629) | ppm by weight | <0.8 |
| Fe (ASTM D5185) | ppb by weight | Not detected |
| Total metals (ASTM D5185) | ppm by weight | Not detected |
| Chlorine (ASTM D7536) | ppb by weight | Not detected |
| Paraffins (UOP990-11) | weight % | 80 |
| Naphthenes (UOP990-11) | weight % | 19 |
| Olefins (UOP990-11) | weight % | Not detected |
| Aromatics (UOP990-11) | weight % | 0.5 |
| Simulated distillation (ASTM D2887) in % | | |
| 0 | ° C. | 25 |
| 5 | ° C. | 40 |
| 10 | ° C. | 61 |
| 30 | ° C. | 94 |
| 50 | ° C. | 123 |
| 70 | ° C. | 157 |
| 90 | ° C. | 179 |
| 95 | ° C. | 258 |
| 100 | ° C. | 350 |

The liquid fraction PI+ has a composition that is compatible with a steam cracking unit, since:
- it does not contain any olefins (monoolefins and diolefins);
- it does not contain any chlorine (content not detected and below the limit required for a steam cracking feedstock)
- it does not contain any iron (Fe) or any metals (content of metals not detected and below the limits required for a steam cracking feedstock, i.e. ≤5.0 ppm by weight and very preferably ≤1 ppm by weight for metals; and also ≤100 ppb by weight for Fe);
- finally, it contains little sulfur (<2 ppm by weight) and little nitrogen (<0.8 ppm by weight), these contents being very much lower than the limits required for a steam cracking feedstock (≤500 ppm by weight, preferably ≤200 ppm by weight for S and N).

The PI+ fraction obtained via the sequence of steps and notably the hydrocracking step c) consists of about 86% of compounds of naphtha type with a boiling point less than or equal to 175° C. This high yield of compounds of naphtha type with a boiling point of less than or equal to 175° C. is obtained by means of the hydrocracking conditions.

The liquid effluent PI+ is sent directly into a steam cracking step h) under the conditions mentioned in Table 8.

TABLE 8 conditions of the steam cracking step

| | | |
|---|---|---|
| Pressure at furnace exit | MPa abs | 0.2 |
| Temperature at furnace exit of PI+ fractions | ° C. | 795 |
| Steam/PI+ fraction ratio | kg/kg | 0.7 |
| Furnace residence time of PI+ fractions | s | 0.3 |

The effluent from the steam cracking furnace is subjected to a separation step which enables recycling of the saturated compounds into the steam cracking furnace and the production of the yields indicated in Table 9 (yield=mass % of product relative to the mass of PI+ fraction upstream of the steam cracking step, noted as % m/m).

TABLE 9 yields for the steam cracking step

| Fractions | | PI+ Fraction |
|---|---|---|
| $H_2$, CO, C1 | % m/m | 7.9 |
| Ethylene | % m/m | 34.1 |
| Propylene | % m/m | 18.6 |
| C4 cut | % m/m | 14.8 |
| Pyrolysis gasoline | % m/m | 19.5 |
| Pyrolysis oil | % m/m | 5.2 |

Considering the yield obtained for the PI+ fraction during the pyrolysis oil treatment process (cf. Table 6), it is possible to determine the overall yields for the products obtained from the steam cracking step relative to the initial feedstock of plastics pyrolysis oil type introduced into step a):

TABLE 10 overall yields for the process of products obtained from the steam cracking step

| Fractions | | PI+ Fraction |
|---|---|---|
| $H_2$, CO, C1 | % m/m | 7.3 |
| Ethylene | % m/m | 31.6 |
| Propylene | % m/m | 17.2 |
| C4 cut | % m/m | 13.7 |
| Pyrolysis gasoline | % m/m | 18.0 |
| Pyrolysis oil | % m/m | 4.8 |

When the liquid fraction PI+ is subjected to a steam cracking step, the process according to the invention makes it possible to achieve overall mass yields of ethylene and propylene, respectively, of 31.6% and 17.2% relative to the mass amount of initial feedstock of plastics pyrolysis oil type.

Furthermore, the specific sequence of steps upstream of the steam cracking step makes it possible to limit the formation of coke and to avoid the corrosion problems which would have appeared had the chlorine not been removed.

Example 2 (in Accordance with the Invention)

In this example, the feedstock to be treated is identical to that described in Example 1 (cf. Table 2).

It undergoes the steps a) of selective hydrogenation, b) of hydrotreatment, c) of hydrocracking and d) of separation, performed under the same conditions as those described in Example 1. The liquid effluent obtained on conclusion of the separation step d) is sent to a fractionation step e) comprising a stripping column and a distillation column for the purpose of obtaining a fraction with a boiling point of less than or equal to 175° C. (PI-175° C. fraction) and a fraction with a boiling point of greater than 175° C. (175° C.+ fraction).

Table 11 gives the overall yields for the various fractions obtained on conclusion of the separation step d) and the fractionation step e) (which comprises a stripping column and a distillation column).

TABLE 11 yields for the various products and fractions obtained at the outlet of the hydrocracking step c)

| | | |
|---|---|---|
| $H_2S$ | % m/m | 0.27 |
| $NH_3$ | % m/m | 0.09 |
| C1 | % m/m | 0.17 |
| C2 | % m/m | 0.26 |
| C3 | % m/m | 1.65 |
| C4 | % m/m | 7.01 |
| PI-175° C. Fraction | % m/m | 84.69 |
| 175° C.+ Fraction | % m/m | 8.00 |
| Total | % m/m | 102.14 |

Treatment of the feedstock according to the steps of the invention and notably the hydrocracking step c) makes it possible to obtain a very high yield of PI-175° C. fraction of naphtha type.

The characteristics of the liquid fractions PI-175° C. and 175° C.+ obtained after the separation step d) and a fractionation step e) are presented in Table 12:

TABLE 12 characteristics of the PI-175° C. and 175° C.+ fractions

| | | PI-175° C. Fraction | 175° C.+ Fraction |
|---|---|---|---|
| Density at 15° C. (ASTM D4052) | g/cm³ | 0.755 | 0.810 |
| Content of: | | | |
| Sulfur (ASTM D5453) | ppm by weight | <2 | <2 |
| Nitrogen (ASTM D4629) | ppm by weight | <0.5 | <3 |
| Fe (ASTM D5185) | ppb by weight | Not detected | 25 |
| Total metals (ASTM D5185) | ppm by weight | Not detected | 1 |
| Chlorine (ASTM D7536) | ppb by weight | Not detected | 25 |
| Paraffins (UOP990-11) | weight % | 80 | 83 |
| Naphthenes (UOP990-11) | weight % | 19.5 | 15 |
| Olefins (UOP990-11) | weight % | Not detected | Not detected |
| Aromatics (UOP990-11) | weight % | 0.5 | 1 |
| Simulated distillation (ASTM D2887) in % | | | |
| 0 | ° C. | 25 | 175 |
| 5 | ° C. | 38 | 185 |
| 10 | ° C. | 59 | 206 |
| 30 | ° C. | 90 | 235 |
| 50 | ° C. | 118 | 265 |
| 70 | ° C. | 140 | 285 |
| 90 | ° C. | 163 | 320 |
| 95 | ° C. | 175 | 344 |
| 100 | ° C. | 180 | 350 |

The liquid fractions PI-175° C. and 175° C.+ both have compositions that are compatible with a steam cracking unit, since:
- they do not contain any olefins (monoolefins and diolefins);
- they have very low contents of chlorine element (respectively, an undetected content and a content of 25 ppb by weight), below the limit required for a steam cracking feedstock;
- the contents of metals, in particular of iron (Fe), are also very low (contents of metals not detected for the PI-175° C. fraction and <1 ppm by weight for the 175° C.+ fraction; contents of Fe not detected for the PI-175° C. fraction and of 25 ppb by weight for the 175° C.+ fraction), which are below the limits required for a steam cracking feedstock (≤5.0 ppm by weight, very preferably ≤1 ppm by weight for metals; ≤100 ppb by weight for Fe);
- finally, they contain sulfur (<2 ppm by weight for the PI-175° C. fraction and <2 ppm by weight for the 175° C.+ fraction) and nitrogen (<0.5 ppm by weight for the PI-175° C. fraction and <3 ppm by weight for the 175° C.+ fraction) with contents that are very much lower than the limits required for a steam cracking feedstock (≤500 ppm by weight, preferably ≤200 ppm by weight for S and N).

The liquid fractions PI-175° C. and 175° C.+ obtained are thus then sent into a steam cracking step h) where the liquid fractions are cracked under various conditions (cf. Table 13).

TABLE 13 conditions of the steam cracking step

| | | |
|---|---|---|
| Pressure at furnace exit | MPa abs | 0.2 |
| Temperature at furnace exit of PI-175° C. fractions | ° C. | 800 |
| Temperature at furnace exit of 175° C.+ fraction | ° C. | 790 |
| Steam/PI-175° C. fraction ratio | kg/kg | 0.6 |
| Steam/175° C.+ fraction ratio | kg/kg | 0.8 |
| Furnace residence time of PI-175° C. fractions | s | 0.3 |
| Furnace residence time of 175° C.+ fractions | s | 0.3 |

The effluents from the various steam cracking furnaces are subjected to a separation step which enables recycling of the saturated compounds into the steam cracking furnaces and the production of the yields presented in Table 14 (yield=mass % of product relative to the mass of each of the fractions upstream of the steam cracking step, noted as % m/m).

TABLE 14 yields for the steam cracking step

| Fractions | | PI-175° C. Fraction | 175° C.+ Fraction |
|---|---|---|---|
| $H_2$, CO, C1 | % m/m | 7.9 | 8.0 |
| Ethylene | % m/m | 34.1 | 34.7 |
| Propylene | % m/m | 18.6 | 18.9 |
| C4 cut | % m/m | 14.8 | 15.1 |
| Pyrolysis gasoline | % m/m | 19.5 | 18.9 |
| Pyrolysis oil | % m/m | 5.2 | 4.4 |

Considering the yields obtained for the various liquid fractions PI-175° C. and 175° C.+ during the pyrolysis oil treatment process at the outlet of the hydrocracking step c) (cf. Table 11), it is possible to determine the overall yields for the products obtained from the steam cracking step relative to the initial feedstock of plastics pyrolysis oil type introduced into step a):

TABLE 15 overall yields for the process of products obtained from the steam cracking step

| Fractions | | PI-175° C. Fraction | 175° C.+ Fraction |
|---|---|---|---|
| $H_2$, CO, C1 | % m/m | 6.7 | 0.6 |
| Ethylene | % m/m | 28.9 | 2.8 |
| Propylene | % m/m | 15.7 | 1.5 |
| C4 cut | % m/m | 12.5 | 1.2 |
| Pyrolysis gasoline | % m/m | 16.5 | 1.5 |
| Pyrolysis oil | % m/m | 4.4 | 0.4 |

When the PI-175° C. and 175° C.+ fractions are sent separately to the steam cracking unit, the process according to the invention makes it possible to achieve overall mass yields of ethylene and propylene, respectively, of 31.7% (=28.9+2.8) and 17.2% (=15.7+1.5) relative to the mass amount of initial feedstock of plastics pyrolysis oil type.

Furthermore, the specific sequence of steps upstream of the steam cracking step makes it possible to limit the formation of coke and to avoid the corrosion problems which would have appeared had the chlorine not been removed.

Example 3 (in Accordance with the Invention)

In this example, the feedstock to be treated is identical to that described in Example 1 (cf. Table 2).

It undergoes the steps a) of selective hydrogenation, b) of hydrotreatment, c) of hydrocracking and d) of separation, performed under the same conditions as those described in Example 1. The liquid effluent obtained on conclusion of the separation step d) is sent to a fractionation step e) comprising a stripping column and a distillation column for the purpose of obtaining a PI-175° C. fraction and a 175° C.+ fraction. The 175° C.+ fraction is partly recycled upstream of the hydrocracking step c) so as to increase the conversion of compounds with a boiling point of greater than 175° C. A small portion of the 175° C. fraction is not recycled upstream of the hydrocracking step c) (purge) so as to avoid the accumulation of polyaromatic compounds which might be coke precursors.

The volume flow rate of 175° C.+ fraction obtained from the fractionation step e) and recycled upstream of the hydrocracking step c) is equal to half the volume flow rate of the liquid effluent obtained from the hydrotreatment step b).

Table 16 gives the overall yields for the various fractions obtained on conclusion of the separation step c) and the fractionation step d) (which comprises a stripping column and a distillation column).

TABLE 16 yields for the various products and fractions obtained at the outlet of the hydrocracking step c)

| $H_2S$ | % m/m | 0.27 |
|---|---|---|
| $NH_3$ | % m/m | 0.09 |
| C1 | % m/m | 0.19 |
| C2 | % m/m | 0.28 |
| C3 | % m/m | 2.50 |
| C4 | % m/m | 9.30 |
| PI-175° C. Fraction | % m/m | 89.40 |
| 175° C.+ Fraction | % m/m | 0.50 |
| Total | % m/m | 102.52 |

Treatment of the feedstock according to the steps of the invention and notably the hydrocracking step c) makes it possible to obtain a very high yield of PI-175° C. fraction of naphtha type, which is further increased relative to Example 1 due to the partial but virtually total recycling of the 175° C.+ fraction into the inlet of the hydrocracking step c).

The characteristics of the liquid fractions PI-175° C. and 175° C.+ obtained after the separation step d) and a fractionation step e) are presented in Table 17:

TABLE 17 characteristics of the PI-175° C. and 175° C.+ fractions

| | | PI-175° C. Fraction | 175° C.+ Fraction |
|---|---|---|---|
| Density at 15° C. (ASTM D4052) | g/cm³ | 0.753 | 0.805 |
| Content of: | | | |
| Sulfur (ASTM D5453) | ppm by weight | <2 | <2 |
| Nitrogen (ASTM D4629) | ppm by weight | <0.5 | <3 |
| Fe (ASTM D5185) | ppb by weight | Not detected | 25 |
| Total metals (ASTM D5185) | ppm by weight | Not detected | 1 |
| Chlorine (ASTM D7536) | ppb by weight | Not detected | <25 |
| Paraffins (UOP990-11) | weight % | 81.5 | 83 |
| Naphthenes (UOP990-11) | weight % | 18 | 15 |
| Olefins (UOP990-11) | weight % | Not detected | 0 |
| Aromatics (UOP990-11) | weight % | 0.5 | 1 |
| Simulated distillation (ASTM D2887) in % | | | |
| 0 | ° C. | 25 | 175 |
| 5 | ° C. | 38 | 185 |
| 10 | ° C. | 59 | 206 |
| 30 | ° C. | 90 | 235 |
| 50 | ° C. | 118 | 265 |
| 70 | ° C. | 140 | 285 |
| 90 | ° C. | 163 | 320 |
| 95 | ° C. | 175 | 344 |
| 100 | ° C. | 180 | 350 |

The liquid fractions PI-175° C. and 175° C.+ both have compositions that are compatible with a steam cracking unit, since:
- they do not contain any olefins (monoolefins and diolefins);
- they have very low contents of chlorine element (respectively, an undetected content and a content of 25 ppb by weight), which are below the limit required for a steam cracking feedstock;
- the contents of metals, in particular of iron (Fe), are also very low (contents of metals not detected for the PI-175° C. fraction and <1 ppm by weight for the 175° C.+ fraction; contents of Fe not detected for the PI-175° C. fraction and of 25 ppb by weight for the 175° C.+ fraction), which are below the limits required for a steam cracking feedstock (≤5.0 ppm by weight, very preferably ≤1 ppm by weight for metals; ≤100 ppb by weight for Fe);

finally, they contain sulfur (<2 ppm by weight for the PI-175° C. fraction and <2 ppm by weight for the 175° C.+ fraction) and nitrogen (<0.5 ppm by weight for the PI-175° C. fraction and <3 ppm by weight for the 175° C.+ fraction) with contents that are very much lower than the limits required for a steam cracking feedstock (≤500 ppm by weight, preferably ≤200 ppm by weight for S and N).

In this Example 2, the 175° C.+ fraction is purged from the unit and is not sent into the steam cracking step.

The liquid fraction PI-175° C. obtained is thus subsequently sent into a steam cracking step h) (cf. Table 18).

TABLE 18 conditions of the steam cracking step

| | | |
|---|---|---|
| Pressure at furnace exit | MPa abs | 0.2 |
| Temperature at furnace exit of PI-175° C. fractions | ° C. | 800 |
| Steam/PI-175° C. fraction ratio | kg/kg | 0.6 |
| Furnace residence time of PI-175° C. fractions | S | 0.3 |

The effluents from the various steam cracking furnaces are subjected to a separation step which enables recycling of the saturated compounds into the steam cracking furnaces and the production of the yields presented in Table 19 (yield=mass % of product relative to the mass of each of the fractions upstream of the steam cracking step, noted as % m/m).

TABLE 19 yields for the steam cracking step

| Fractions | | PI-175° C. Fraction |
|---|---|---|
| $H_2$, CO, C1 | % m/m | 7.9 |
| Ethylene | % m/m | 34.3 |
| Propylene | % m/m | 18.7 |
| C4 cut | % m/m | 14.9 |
| Pyrolysis gasoline | % m/m | 19.3 |
| Pyrolysis oil | % m/m | 4.9 |

Considering the yields obtained for the liquid fraction 175° C.+ during the pyrolysis oil treatment process at the outlet of the hydrocracking step (cf. Table 16), it is possible to determine the overall yields for the products obtained from the steam cracking step relative to the initial feedstock of plastics pyrolysis oil type introduced into step a):

TABLE 20 overall yields for the process of products obtained from the steam cracking step

| Fractions | | PI-175° C. Fraction |
|---|---|---|
| $H_2$, CO, C1 | % m/m | 7.1 |
| Ethylene | % m/m | 30.7 |
| Propylene | % m/m | 16.7 |
| C4 cut | % m/m | 13.3 |

TABLE 20-continued overall yields for the process of products obtained from the steam cracking step

| Fractions | | PI-175° C. Fraction |
|---|---|---|
| Pyrolysis gasoline | % m/m | 17.2 |
| Pyrolysis oil | % m/m | 4.4 |

When the PI-175° C. fraction is sent separately to the steam cracking unit, the process according to the invention makes it possible to achieve overall mass yields of ethylene and propylene, respectively, of 30.7% and 16.7% relative to the mass amount of initial feedstock of plastics pyrolysis oil type.

Furthermore, the specific sequence of steps upstream of the steam cracking step makes it possible to limit the formation of coke and to avoid the corrosion problems which would have appeared had the chlorine not been removed.

Example 4 (not in Accordance with the Invention)

In this example, the feedstock to be treated is identical to that described in Example 1 (cf. Table 2).

It undergoes the steps a) of selective hydrogenation, b) of hydrotreatment and d) of separation, performed under the same conditions as those described in Example 1. In this example not in accordance with the invention, the effluent obtained from the hydrotreatment step is not subjected to a hydrocracking step. The liquid effluent obtained on conclusion of the separation step d) constitutes the PI+ fraction.

The yields for the various products and for the various fractions obtained at the outlet of the hydrotreatment step b) are indicated in Table 21 (the yields corresponding to the ratios of the mass amounts of the various products obtained relative to the mass of feedstock upstream of step a), expressed in percentages and noted as % m/m).

TABLE 21 yields for the various products and fractions obtained at the outlet of the hydrotreatment step b)

| | | |
|---|---|---|
| $H_2S$ | % m/m | 0.27 |
| $NH_3$ | % m/m | 0.09 |
| C1 | % m/m | 0.01 |
| C2 | % m/m | 0.02 |
| C3 | % m/m | 0.09 |
| C4 | % m/m | 0.38 |
| PI+ Fraction | | 99.55 |
| Total | % m/m | 100.05 |

The characteristics of the PI+ fraction (which corresponds to the liquid effluent) obtained after the separation step d) are presented in Table 22:

TABLE 22 characteristics of the PI+ fraction

| | | PI+ Fraction |
|---|---|---|
| Density at 15° C. (ASTM D4052) | lg/cm³ | 0.803 |
| Content of: | | |
| Sulfur (ASTM D5453) | ppm by weight | <2 |
| Nitrogen (ASTM D4629) | ppm by weight | <0.8 |
| Fe (ASTM D5185) | ppb by weight | Not detected |
| Total metals (ASTM D5185) | ppm by weight | Not detected |
| Chlorine (ASTM D7536) | ppb by weight | Not detected |
| Paraffins (UOP990-11) | weight % | 66 |
| Naphthenes (UOP990-11) | weight % | 32 |
| Olefins (UOP990-11) | weight % | Not detected |
| Aromatics (UOP990-11) | weight % | 2 |
| Simulated distillation (ASTM D2887) in % | | |
| 0 | ° C. | 26 |
| 5 | ° C. | 55 |
| 10 | ° C. | 93 |
| 30 | ° C. | 157 |
| 50 | ° C. | 226 |
| 70 | ° C. | 304 |
| 90 | ° C. | 390 |
| 95 | ° C. | 397 |
| 100 | ° C. | 431 |

The PI+ fraction obtained via the sequence of steps a), b) and d) consists of about 35% of compounds of naphtha type with a boiling point less than or equal to 175° C. This low yield of compounds of naphtha type with a boiling point of less than or equal to 175° C. is due to the absence of the hydrocracking step in this example not in accordance.

The liquid effluent fraction PI+ is sent directly into a steam cracking step h) under the conditions mentioned in Table 23.

TABLE 23 conditions of the steam cracking step

| Pressure at furnace exit | MPa abs | 0.2 |
|---|---|---|
| Temperature at furnace exit of PI+ fraction | ° C. | 795 |
| Steam/PI+ fraction ratio | kg/kg | 0.7 |
| Furnace residence time of PI+ fraction | S | 0.3 |

The effluent from the steam cracking furnace is subjected to a separation step which enables recycling of the saturated compounds into the steam cracking furnace and the production of the yields indicated in Table 24 (yield=mass % of product relative to the mass of PI+ fraction upstream of the steam cracking step, noted as % m/m).

TABLE 24 yields for the steam cracking step

| Fractions | | PI+ Fraction |
|---|---|---|
| $H_2$, CO, C1 | % m/m | 8.1 |
| Ethylene | % m/m | 34.8 |
| Propylene | % m/m | 19.0 |
| C4 cut | % m/m | 15.1 |
| Pyrolysis gasoline | % m/m | 18.8 |
| Pyrolysis oil | % m/m | 4.2 |

Considering the yield obtained for the PI+ fraction during the pyrolysis oil treatment process at the outlet of the hydrotreatment step b) (cf. Table 21), it is possible to determine the overall yields for the products obtained from the steam cracking step relative to the initial feedstock of plastics pyrolysis oil type introduced into step a):

TABLE 25 overall yields for the process of products obtained from the steam cracking step

| Fractions | | PI+ Fraction |
|---|---|---|
| $H_2$, CO, C1 | % m/m | 8.1 |
| Ethylene | % m/m | 34.6 |
| Propylene | % m/m | 18.9 |
| C4 cut | % m/m | 15.0 |
| Pyrolysis gasoline | % m/m | 18.7 |
| Pyrolysis oil | % m/m | 4.2 |

When the liquid fraction PI+ is subjected to a steam cracking step, the process according to the invention makes it possible to achieve overall mass yields of ethylene and propylene, respectively, of 34.6% and 18.9% relative to the mass amount of initial feedstock of plastics pyrolysis oil type.

The invention claimed is:

1. A process for treating a feedstock comprising a plastics pyrolysis oil comprising chlorinated compounds, said process comprising:
  a) a selective hydrogenation step performed in a reaction section fed at least with said feedstock containing chlorinated compounds, said feedstock being maintained in liquid phase, and a gas stream comprising hydrogen, in the presence of at least one selective hydrogenation catalyst, at a temperature of between 10° and 280° C., a partial pressure of hydrogen of between 1.0 and 10.0 MPa abs, and an hourly space velocity of between 0.3 and 10.0 h$^{-1}$, to obtain a hydrogenated effluent with a reduced content of diolefins, wherein an amount of the gas stream comprising hydrogen feeding said reaction section of stage a) is such that the hydrogen coverage is between 1 and 50 Nm³ of hydrogen per m³ of feedstock;
  b) a hydrotreatment step performed in a hydrotreatment reaction section, containing at least one fixed-bed reactor containing n catalytic beds, n being an integer greater than or equal to 1, each comprising at least one hydrotreatment catalyst, said hydrotreatment reaction section being fed at least with said hydrogenated effluent obtained from step a) and a gas stream comprising hydrogen, said hydrotreatment reaction section having a temperature of between 25° and 430° C., a partial pressure of hydrogen of between 1.0 and 10.0 MPa abs, and an hourly space velocity of between 0.1 and 10.0 h$^{-1}$, to obtain a hydrotreated effluent;
  c) a hydrocracking step performed in a hydrocracking reaction section, containing at least one fixed-bed reactor containing n catalytic beds, n being an integer greater than or equal to 1, each comprising at least one hydrocracking catalyst, said hydrocracking reaction section being fed at least with said hydrotreated effluent obtained from step b) and a gas stream comprising hydrogen, said hydrocracking reaction section having a temperature of between 25° and 480° C., a partial pressure of hydrogen of between 1.5 and 25.0 MPa abs, and an hourly space velocity of between 0.1 and 10.0 $h^{-1}$, to obtain a hydrocracked effluent;

d) a separation step, fed with the hydrocracked effluent obtained from step c) and an aqueous solution, said step being performed at a temperature of between 5° and 370° C., to obtain at least one gaseous effluent, an aqueous effluent and a hydrocarbon-based effluent, wherein the separation stage d) comprises an injection of an aqueous solution into the hydrocracking effluent resulting from stage c), upstream of the separation step; and e) fractionating all or a portion of the hydrocarbon-based effluent obtained from step d) to obtain at least one gas stream and at least two liquid hydrocarbon-based streams, which include a naphtha cut comprising compounds with a boiling point of less than or equal to 175° C. and a hydrocarbon cut comprising compounds with a boiling point of greater than 175° C.

2. The process according to claim 1, which also comprises a recycling step f) in which at least a fraction of the cut comprising compounds with a boiling point of greater than 175° C. obtained from the fractionation step e) is sent into the hydrocracking step c).

3. The process according to claim 1, which also comprises a recycling step g) in which a fraction of the hydrocarbon-based effluent obtained from the separation step d) or a fraction of the naphtha cut comprising compounds with a boiling point of less than or equal to 175° C. obtained from the fractionation step e) is sent into the selective hydrogenation step a) and/or the hydrotreatment step b).

4. The process according to claim 1, which also comprises a recycling step f) in which at least a fraction of the cut comprising compounds with a boiling point of greater than 175° C. obtained from the fractionation step e) is sent into the hydrocracking step c), and which also comprises a recycling step g) in which a fraction of the hydrocarbon-based effluent obtained from the separation step d) or a fraction of the naphtha cut comprising compounds with a boiling point of less than or equal to 175° C. obtained from the fractionation step e) is sent into the selective hydrogenation step a) and/or the hydrotreatment step b), and in which an amount of the recycle stream from steps f) and/or g) is adjusted so that a weight ratio between the recycle stream and the feedstock comprising the plastics pyrolysis oil is less than or equal to 10.

5. The process according to claim 1, further comprising a step a0) of pretreating the feedstock comprising a plastics pyrolysis oil, said pretreatment step being performed upstream of the selective hydrogenation step a) and comprises a filtration step and/or a step of washing with water and/or an adsorption step.

6. The process according to claim 1, in which the reaction section of step a) or b) contains at least two reactors functioning in permutable mode.

7. The process according to claim 1, in which a stream containing an amine is injected upstream of step a).

8. The process according to claim 1, in which said selective hydrogenation catalyst comprises a support selected from the group consisting of alumina, silica, silica-aluminas, magnesia, clays and mixtures thereof, and a hydro-dehydrogenating function comprising either at least one group VIII element and at least one group VIB element, or at least one group VIII element.

9. The process according to claim 1, in which said at least one hydrotreatment catalyst comprises a support selected from the group consisting of alumina, silica, silica-aluminas, magnesia, clays and mixtures thereof, and a hydro-dehydrogenating function comprising at least one group VIII element and/or at least one group VIB element.

10. The process according to claim 1, in which said hydrocracking catalyst comprises a support selected from the group consisting of halogenated aluminas, combinations of boron and aluminium oxides, amorphous silica-aluminas and zeolites, and a hydro-dehydrogenating function comprising at least one group VIB metal selected from the group consisting of chromium, molybdenum, tungsten, and mixtures thereof, and/or at least one group VIII metal selected from the group consisting of iron, cobalt, nickel, ruthenium, rhodium, palladium and platinum.

11. The process according to claim 10, in which said zeolite is selected from Y zeolites, alone or in combination; with other zeolites selected from the group consisting of beta, ZSM-12, IZM-2, ZSM-22, ZSM-23, SAPO-11, ZSM-48, ZBM-30 zeolites and mixtures thereof.

12. The process according to claim 1, in which at least one of the two liquid hydrocarbon-based streams obtained from step e) is totally or partly sent into a steam cracking step h) performed in at least one pyrolysis furnace at a temperature of between 70° and 900° C. and at a pressure of between 0.05 and 0.3 MPa relative.

13. The process according to claim 1, in which the naphtha cut comprising compounds with a boiling point of less than or equal to 175° C. obtained from step e) is fractionated into a heavy naphtha cut comprising compounds with a boiling point of between 8° and 175° C. and a light naphtha cut comprising compounds with a boiling point of less than 80° C., at least a portion of said heavy cut being sent into an aromatic complex including at least one naphtha reforming step.

14. The process according to claim 13, in which at least a portion of the light naphtha cut is sent into a steam cracking step h).

* * * * *